(12) United States Patent
Devore et al.

(10) Patent No.: US 9,574,041 B2
(45) Date of Patent: Feb. 21, 2017

(54) GRAFT POLYMERS FOR ENHANCED INTRACELLULAR DELIVERY OF ANTISENSE MOLECULES

(71) Applicant: Rutgers, The State University of New Jersey, New Brunswick, NJ (US)

(72) Inventors: David Devore, Langhorne, PA (US); Charles Roth, Princeton, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/629,013

(22) Filed: Feb. 23, 2015

(65) Prior Publication Data

US 2015/0266989 A1    Sep. 24, 2015

Related U.S. Application Data

(62) Division of application No. 12/744,824, filed as application No. PCT/US2008/084995 on Nov. 26, 2008, now Pat. No. 8,962,757.

(60) Provisional application No. 60/990,606, filed on Nov. 27, 2007.

(51) Int. Cl.
| | |
|---|---|
| C08G 73/02 | (2006.01) |
| C08F 265/02 | (2006.01) |
| A61K 31/70 | (2006.01) |
| C08G 81/02 | (2006.01) |
| A61K 47/32 | (2006.01) |

(52) U.S. Cl.
CPC ............ *C08F 265/02* (2013.01); *A61K 31/70* (2013.01); *A61K 47/32* (2013.01); *C08G 81/025* (2013.01)

(58) Field of Classification Search
None
See application file for complete search history.

(56) References Cited

PUBLICATIONS

Peddada et al (Journal of Controlled Release 140 (2009) 134-140).*
Huntsman, (The Jeffamine® Polyetheramines, Copyright © 2007 Huntsman Corporation), accessed at http://www.huntsman.com/portal/page/portal/performance_products/Media%20Library/global/files/jeffamine_polyetheramines.pdf) on Feb. 16, 2016.*
Hourdet et al (Polymer 38(10): 2535-2547, 1997).*

* cited by examiner

*Primary Examiner* — Richard Schnizer
(74) *Attorney, Agent, or Firm* — Fox Rothschild LLP

(57) ABSTRACT

Innovative graft polymers designed for the efficient delivery of antisense molecules into biological cells and for maintaining the biological activity of these molecules while in serum and other aqueous environments are provided. Such polymers may comprise an anionic graft polymer comprising an anionic polymer backbone with pendant carboxylic acid groups and pendant chains comprising amphipathic or hydrophilic polymers covalently bonded to a portion of said pendant carboxylic acid groups. Antisense molecule delivery vectors comprising such polymers in combination with cationic agents for delivery of antisense molecules are also disclosed.

14 Claims, 23 Drawing Sheets

D: DOTAP; O: ODN; P: PPAA; P-JEFFAMINE x%: JEFFAMINE 2K CONJUGATED TO PPAA OF x% GRAFTING DENSITY

D: DOTAP; O: ODN; P: PPAA; P-JEFFAMINE x%: JEFFAMINE 2K CONJUGATED TO PPAA OF x% GRAFTING DENSITY

GRAFT POLYMERS FOR ENHANCED INTRACELLULAR DELIVERY OF ANTISENSE MOLECULES

CROSS-REFERENCE TO RELATED APPLICATIONS

This application is a divisional of U.S. patent application Ser. No. 12/744,824, filed on May 26, 2010, which is the U.S. National Stage of International Patent Application No. PCT/US08/84995, filed on Nov. 26, 2008, which claims the benefit of U.S. Provisional Application Ser. No. 60/990,606, filed on Nov. 27, 2007, the disclosures of which are incorporated herein by reference in their entireties.

FIELD OF THE INVENTION

This invention relates to materials and methods for intracellular delivery of antisense molecules.

BACKGROUND OF INVENTION

The ability of exogenously administered nucleotide molecules to mediate gene silencing was discovered nearly 30 years ago. Ever since, this technology has been utilized as a research tool to study gene function, and over time it has been developed for treatment of diseases arising from the abnormal over-expression or over-activity of a particular gene, such as cancer, autoimmune and cardiovascular diseases, wound healing and viral infections. This technology, referred to herein as antisense therapeutics, includes a range of technologies differentiated by the approaches they use to break down the mRNA. Approaches currently generating interest include, for example, RNA interference (RNAi), micro-RNA, and the use of conventional antisense deoxynucleotide technologies.

Further progress in this field requires improvement in the systemic and cellular delivery of these antisense therapeutics to their targets. Some of the barriers at the systemic level include survival against unfavorable interactions with serum proteins present in the bloodstream, avoidance of accumulation in non-target organs such as lung, liver and kidney, and targeting of the diseased or infected cells. Once the antisense therapeutics have overcome these barriers, they must maneuver their way into the target cell and finally to the target mRNA within the cell. Some of the challenges to antisense therapeutics delivery at the cellular level include efficient entry into the cell, escape from degradative lysosomes, and release into the cytoplasm.

While viral vectors are also being used for delivery of such antisense therapeutics and gene delivery, safety concerns persist. Although iterative design of non-viral vectors has endowed them with attributes for overcoming some of the systemic and cellular barriers in the delivery of antisense therapeutics, their delivery efficiencies are generally too low and their cytotoxicities are generally too high. A major barrier to the intracellular delivery of antisense therapeutics is their sequestration in endosomes, which eventually fuse with lysosomes, leading to degradation of their contents.

Accordingly, there is a need in the art for methods and materials that improve intracellular delivery of antisense therapeutics.

SUMMARY OF INVENTION

First aspect of the invention provides innovative graft polymers designed for the efficient delivery of antisense molecules into biological cells and for maintaining the biological activity of these molecules while in serum and other aqueous environments. Such polymers may comprise an anionic graft polymer comprising an anionic polymer backbone with pendant carboxylic acid groups and pendant chains comprising amphipathic or hydrophilic polymers covalently bonded to a portion of said pendant carboxylic acid groups. The instant polymers preferably have a graft density of between about 1 and about 25 mole percent, more preferably between about 5 and about 25 mole percent, and most preferably between about 20 to about 25 mole percent.

Suitable anionic backbone polymers include, but are not limited to, polyanhydrides, poly(acrylic acids), poly(alkylacrylic acids), carboxymethylcellulose, polyglutamic acids, polyaspartic acids, vinyl copolymers, or combinations thereof. In the preferred embodiments the backbone of the instant polymer comprises poly (propyl acrylic acid). Suitable polymers for use as pendant chains, include but are not limited to, poly(etheramines), polyalkylene oxides, or combinations thereof.

In one specific embodiment, such polymers may comprise a backbone comprising a poly(alkyl acrylic acid); and one or more poly(ether amine) pendant chains covalently attached to said polymer backbone via said acrylic acid groups predominantly comprising ethylene oxide repeating units, wherein said polymer has a graft density between about 1 and about 25 mole percent.

A second aspect of the invention provides a vector for intracellular delivery of antisense molecules comprising a graft polymer as described above and at least one cationic agent for delivery of antisense molecule. Suitable cationic agents for delivery of antisense mole include, but are not limited to, surfactants, liposomes, peptides, polymers, micelles, nanoparticles or combinations thereof. The delivery vector may also include an antisense molecule, such as antisense oligonucleotide or an siRNA. The delivery vector including an antisense molecule has a charge ratio of 1 and a particle size of about 215 nm to about 300 nm.

A third aspect of the invention provides a pharmaceutical composition comprising the delivery vector as described above and a pharmaceutically acceptable carrier. The composition may further comprise an antisense molecule, such as antisense oligonucleotide or a short interfering RNA (siRNA).

A fourth aspect of the invention provides a method of treatment cancer. Such method includes silencing oncogenic expression in cancer cells by administering to a patient a therapeutically effective amount of the delivery vector as described above further comprising an siRNA targeted to an anti-apoptotic gene, such as BCL-2. Preferably, the concentration of siRNA is between about 40 and about 50 nM.

DETAILED DESCRIPTION OF THE INVENTION

Figure 1:
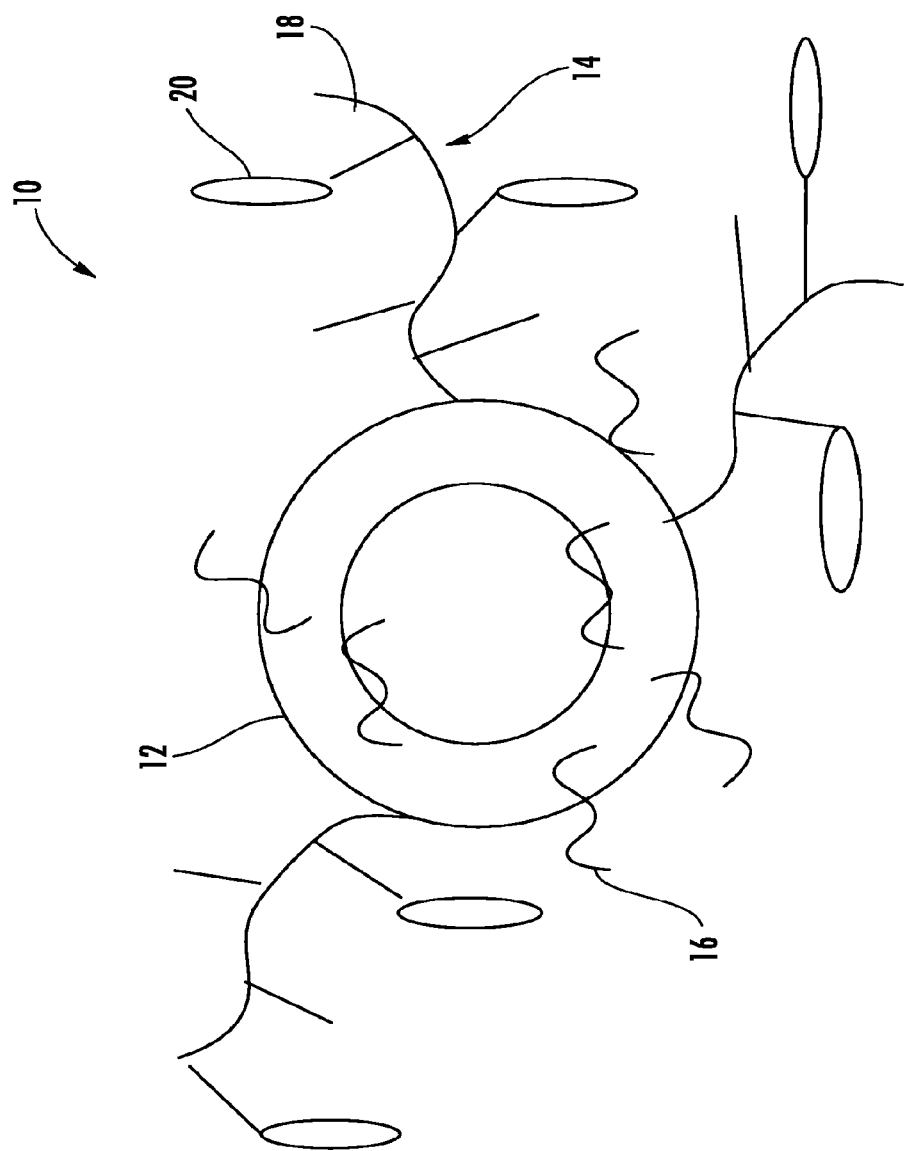
FIG. 1 presents a diagram of a delivery complex.

One aspect of the invention provides innovative graft polymers designed for the efficient delivery of antisense molecules into biological cells and for maintaining the biological activity of the antisense molecules while in serum and other aqueous environments. Such graft polymers may comprise an anionic graft polymer comprising an anionic polymer backbone, refereed herein as backbone polymer, with pendant carboxylic acid groups and pendant chains comprising amphipathic or hydrophilic polymers, refereed herein as pendant chain polymers, covalently bonded to a portion of said pendant carboxylic acid groups.

Suitable backbone polymers include, but are not limited to, polyanhydrides, poly(acrylic acids) or a poly(alkylacrylic acids), anionic polysaccharides such as carboxymethylcellulose, anionic polypeptides such as polyglutamic acid and polyaspartic acid, vinyl copolymers comprised of monomers such as alkyl acrylates, alkyl methacrylates, AMPS, vinyl alcohol, and vinyl acetate, or combinations thereof. Preferably, the backbone polymer comprises poly(propyl acrylic acid).

The term "hydrophilic polymer," as used herein, means any macromolecule (molecular weights of 200 daltons and greater) which exhibits an affinity for or attraction to water molecules and which comprises multiple instances of an identical subunit ("monomer") connected to each other in chained and/or branched structures. The hydrophilic polymer component may be a synthetic or naturally occurring hydrophilic polymer.

Naturally occurring hydrophilic polymers include, but are not limited to: proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives.

Useful synthetic hydrophilic polymers include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly (acryl-amides) such as polyacrylamide per se, poly(methacrylamide), poly(dimethylacrylamide), and poly(N-isopropyl-acrylamide); poly(olefinic alcohol) s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly (ethyloxazoline; and polyvinylamines.

Preferred embodiments utilize polyethyleneglycol (PEG), also known as poly(ethylene oxide) (PEO), having a molecular weight of about 2 kDA and a general formula (II).

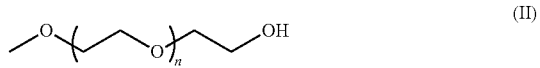

(II)

The term "amphipathic polymer," as used herein, refers to any macromolecule (molecular weights of 200 daltons and greater) which have localized quantum variations in charge giving rise to polar substructures and non-polar substructures. The polar substructures evidence an affinity for or attraction to other polar molecular structures such as water molecules (hydrophilic), while the nonpolar substructures exhibit an affinity or attraction for nonpolar molecules such as lipids, oils, greases, fats, etc. (lipophilic). Suitable amphipathic polymers include, but are not limited to, polyetherester copolymers such as polyethylene glycol and polylbutylene terephthalate copolymers, polyethylene glycol and polypropylencoxide copolymers, polyethylene glycol and polypropylene glycol block copolymers.

The amphipathic polymers also include a family of polyetheramines known as Jeffamine®. These polyetheramines contain primary amino groups attached to the end of a polyester backbone, which is typically based on propylene oxide (PO), ethylene oxide (EO), or a mixture thereof. The Jeffamine® family includes monamines, diamines, triamines and secondary amines. Jeffamine® may be procured from Huntsman Corporation, headquartered in The Woodlands, Tex. By way of non-limiting example, some embodiments may employ a Jeffamine® Monoamine having a molecular weigh of about 2 kDA, PO/PE ratio of 10/31 and a general formula II:

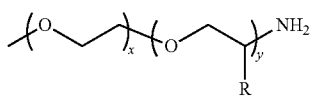

(III)

wherein R is H for EO or CH₃ for PO.

The instant graft polymers may be synthesized by reacting carboxylic acid groups of the backbone polymer with the end group of the pendant chain polymers. Suitable methods for synthesizing the instant graft polymers are disclosed, for example, in Moore, J., Stupp, S I. *Journal of Organic Chemistry* 1990, 55, 3374; and Hourdet D, L. A. F., Audebert R. *Polymer* 1997, 38, 2535-2547. In general, a backbone polymer may be added to a polar aprotic solvent, such as Dimethyl sulfoxide (DMSO), along with a catalyst, such as DPTs or HoBt 9 and a pendant chain polymer. The amount of graft chain polymer may be in a slight molar excess required to achieve the desired amount of the graft chain polymer attached to the backbone. A carboxyl activating agent, such as EDCI, may be added to the mixture after stirring the mixture for a short period of time. The reaction is then allowed to proceed and is driven to completion with subsequent additions of the carboxyl activating agent. The mixture may then be dialyzed against deionized water before converting the polymer into a form suitable for storage, such as by lyophilizing the dialyzed solution.

The amount of the graft chain polymers may be calculated based on the target graft density. The term "graft density," as used herein, refers to the average percent on a molar basis of pendant carboxyl groups on the backbone of the graft polymer which react with the end group of the pendant chain polymers. The graft density for instant graft polymers is preferably between about 1 to about 25 mole percent, more preferably between about 5 and 25 mole percent, and most preferably between about 20 and about 25 mole percent. Alternatively, the amount of the graft chain polymer may be calculated based on weight percent. Preferably, the amount of the pendant chain polymer is sufficient to mask the hydrophobic carboxyl groups of the backbone. In some embodiments, the instant graft polymer comprise greater than 50 percent weight of the pendant chain polymer.

By way of non-limiting example, a graft polymer may comprise a backbone comprising a poly(alkyl acrylic acid) and one or more poly(ether amine) pendant chains covalently attached to said polymer backbone via said acrylic acid groups. The poly(ether amine) may predominantly comprise ethylene oxide repeating units. Preferably, such polymer has a graft density between about 1 and about 25 mole percent.

Another aspect of the invention provides vectors for delivery of antisense molecules into cells in vivo. The term "vector," as used herein, refers to a carrier into which an antisense molecule may be inserted or to which an antisense molecule may be attached for introduction into a cell. Instant vectors may comprise the graft polymers described above bound to at least one cationic agent. The term "cationic agent," as used herein, refers to a substance suitable for delivery of antisense molecules and having a positive net charge at physiological pH. Suitable cationic agents for delivery of antisense molecules include, but are not limited to cationic, lipids, surfactants, liposomes, micelles peptides, polymers, nanoparticles or combinations thereof.

Cationic liposomes or micelles can be prepared using mixtures including one or more lipids containing a cationic side group in sufficient quantity such that the liposomes or micelles formed from the mixture possess a net positive charge which will ionically bind negatively charged compounds. Suitable lipids include, but are not limited to, DODAC, DOTMA, DDAB, DOTAP, DC-Chol and DMRIE. Additionally, a number of commercial preparations of cationic liposomes are available which include, for example, LIPOFECTIN® comprising DOTMA and DOPE, and LIPOFECTAMINE® comprising DOSPA and DOPE.

Cationic surfactants include, but are not limited to, quaternary ammonium salts, for example, didodecyldimethylammonium bromide (DDDAB), alkyltrimethylammonium bromides such as hexadecyltrimethylammonium bromide (HDTAB), dodecyl-trimethylammonium bromide (DT-MAB), myristyltrimethylammonium bromide (MTMAB), or palmityl trimethylammonium bromide, or N-alkylpyridinium salts, or tertiary amines, for example, cholesteryl-3β-N-(dimethyl-aminoethyl)-carbamate or mixtures thereof. Cationic peptides may be selected from naturally occurring or recombinant or synthetic peptide produced by known means. Examples of suitable cationic peptides include, but are not limited to, magainins, colicins, alamethicin, pexiganan or MSI-78, and other MSI peptides like MSI-843 and MSI-594, polyphemusin, human antimicrobial peptide, LL-37, defensins and protegrins. Finally, suitable examples of cationic polymers include, but are not limited to, acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethyl-ethylene.

Alternatively or additionally, the vectors may comprise the graft polymers in combination with organic or inorganic nanoparticles. It is desirable to use nanoparticles that biocompatible and hydrophilic and range in size between about 10 nm and 300 nm, and more preferably between about 50 nm and 150 nm. Although not necessary, biodegradable or resorbable nanoparticles are preferred.

The instant delivery vectors form ternary delivery complexes with antisense molecules. The term "antisense molecule," as used herein, refers to ribonucleic acid sequences, modified ribonucleic acid sequences, or DNA sequences encoding said ribonucleic acid sequences, which cause RNA interference and/or, via other biological mechanisms, decrease or silence expression of the target gene. The antisense molecules are sufficiently complementary to the sequence of DNA or mRNA encoding a target gene so as to have the proper antisense or interfering property. Suitable antisense molecules include, without limitations, antisense oligodeoxynucleotides, shRNAs, siRNAs, miRNAs, and DNA-RNA hybrids. RNAi agent synthesis and their use is well known in the art. (see e.g. Caniggia (1999) J Clin Invest., Matveeva (2000) Nucleic Acid Res; Elbashir et al. (2001) EMBO J.). The term "target gene," as used herein, refers to a gene whose expression is to be selectively inhibited or silenced through RNA interference because its expression or activity is associated with a particular disease. For example, cancer may arise from abnormal expression or activity of a gene associated with the inhibition or prevention of apoptosis, such as Bcl-2, Bcl-XL, Bcl-w, Mcl-1, and/or A1. Accordingly, in one embodiment, the antisense molecule is a siRNA targeted to an anti-apoptotic gene.

These complexes may be self-assembled from their individual components through electrostatic interactions. Generally, equal volumes of the cationic agent for delivery of antisense molecules and the antisense molecule may be incubated at room temperature for about 30 minutes, before adding of the instant graft polymer to produce the desired charge ratio of the complex. The term "charge ratio," as used herein, refers to a ratio of the moles of amine groups of the cationic agent to the number of moles of phosphate groups of the antisense molecule, carboxylic groups of the graft polymer, or a sum thereof. Preferably, the charge ratio of the complexes disclosed herein is between about 0.5 and 2, and more preferably about 1.

FIG. 1 presents an example of the instant delivery complex 10 comprising a cationic agent 12, graft polymers 14, and antisense molecules 16. Each graft polymer 14 comprises a backbone polymer 18 and pendant chain polymer 20. Despite the overall charge neutrality of the complex, the instant graft polymers do not induce aggregate formations. Thus, the instant delivery complexes form stable particles in various buffer solutions with particle sizes ranging from about 25 to about 300 nm, and more preferably between about 215 to about 300 nm. Furthermore, addition of instant graft polymers preferably does not alter binding ability of the cationic agents and antisense molecules.

Yet another aspect provides pharmaceutical compositions comprising delivery vectors bound to antisense molecules, as described above, and one or more pharmaceutically acceptable carriers. The term "pharmaceutically acceptable carrier," as used herein, refers to a non-toxic, inert solid, semi-solid or liquid filler, diluent, encapsulating material or formulation auxiliary of any type. Many different pharmaceutically acceptable carriers are known and disclosed, for example, in Remington's Pharmaceutical Sciences, Lippincott Williams & Wilkins; 21 edition (May 1, 2005). Some examples of pharmaceutically acceptable carriers include, but are not limited to, sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations.

In addition, the instant compositions may include excipients such as solvents, binders, fillers, disintegrants, lubricants, suspending agents, surfactants, viscosity increasing agents, buffering agents, antimicrobial agents, among others. The acceptable excipients and methods for making various compositions are known and may be found, for example, in Remington's Pharmaceutical Sciences, Lippincott Williams & Wilkins, 21$^{st}$ edition, (May 1, 2005).

The compositions may be prepared in a solid or liquid form for oral, parenteral, enteral or topical administration. Suitable examples of solid forms include, but are not limited to, tablets, pills, lozenges, dragees, powders, granules, capsules, etc. Solid forms may or may not include a pharmaceutically acceptable carrier. Suitable examples of liquid forms include, but are not limited to, solutions, dispersions, emulsions, gels, syrups, slurries, suspensions, and so forth. Liquid formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Instant compositions may be delivered by rapid release systems, modified release systems, or systems which may provide a part of the dose by modified release and the rest by rapid release. Various approaches are known and used in the art to prepare immediate release systems or modified release systems. Many of these methods are disclosed, for example, in Remington's Pharmaceutical Sciences, Lippincott Williams & Wilkins; 21 edition (May 1, 2005). Examples of immediate release systems include, but are not limited to, conventional tablets or capsules, or solutions. Examples of modified release systems include, but are not limited to, coated pellets, tablets or capsules; multiple unit or multiparticulate systems in the form of microparticles or nonoparticles, microspheres or pellets comprising the active agent; formulations comprising dispersions or solid solutions of active compound in a matrix, which may be in the form of a wax, gum, fat, or polymer; devices, in which drug is attached to an ion exchange resin, which provides for gradual release of drug by way of influence of other ions present in the gastrointestinal tract, for example, the acid environment of the stomach; devices, such as osmotic pumps, in which release rate of drug is controlled by way of its chemical potential; systems in which drug is released by diffusion through membranes, including multilayer systems, and so forth.

In preferred embodiments, the instant compositions are prepared for parenteral administration. Parenteral administration is generally characterized by a subcutaneous, intramuscular, or intravenous injection. Compositions of instants delivery complexes for parenteral administration may be prepared as liquid solutions or suspensions, solid forms suitable for solution or suspension in liquid prior to injection, or as emulsions.

Another aspect is directed to methods for treating a subject who is affected by a disease or at risk of developing a disease that may be treated by inhibiting or silencing a target gene, i.e, a gene associated with the disease. Such methods comprise administering to a patient a therapeutically effective amount of a composition comprising one or more delivery vectors, as described above, bound to one or more antisense molecules designed to interfere with the target gene. Disease that can be treated by the instant methods include, but are not limited to, cancer, neurological diseases, genetic disorders and wounds.

The terms "silence," "decrease the expression of" and "inhibit the expression of", in as far as they refer to a target gene, herein refer to the at least partial suppression of the expression of the target gene, as manifested by a reduction of the amount of mRNA transcribed from the target gene which may be isolated from a first cell or group of cells in which the target gene is transcribed and which has or have been treated such that the expression of the target gene is inhibited, as compared to a second cell or group of cells substantially identical to the first cell or group of cells but which has or have not been so treated (control cells). Alternatively, the degree of silencing, decreasing or inhibiting may be given in terms of a reduction of a parameter that is functionally linked to target gene transcription, e.g. the amount of protein encoded by the target gene which is secreted by a cell, or the number of cells displaying a certain phenotype, e.g. apoptosis.

The term "therapeutically effective amount" means a quantity of the active agent which, when administered to a patient, is sufficient to result in an improvement in patient's condition. The improvement does not mean a cure and may include only a marginal change in patient's condition. It also includes an amount of the active agent that prevents the condition or stops or delays its progression. The term "treating" or "treatment" refers to executing a protocol, which may include administering one or more drugs to a patient (human or otherwise), in an effort to alleviate signs or symptoms of the disease. Alleviation can occur prior to signs or symptoms of disease appearing, as well as after their appearance. Thus, "treating" or "treatment" includes "preventing" or "prevention" of the disease. In addition, "treating" or "treatment" does not require complete alleviation of signs or symptoms, does not require a cure, and specifically includes protocols which have only a marginal effect on the patient.

In one specific embodiment, methods are provided for silencing oncogenic expression in cancer cells. This can be achieved by administering to a patient who is affected or at risk of developing cancer a therapeutically effective amount of composition comprising one or more antisense molecules designed to silence oncogenic expression in cancer cells in conjunction with instant delivery vectors. The antisense molecules may target a single gene or multiple genes associated with cancer.

In some embodiments, the antisense may comprise a siRNA targeted to an anti-apoptotic gene, such as Bcl-2, Bcl-XL, Bcl-w, Mcl-1, and/or A1. Additional examples of genes which can be targeted include, without limitation, an oncogene (Hanahan, D. and R. A. Weinberg, Cell (2000) 100:57; and Yokota, J., Carcinogenesis (2000) 21(3):497-503); genes of proteins that are involved in metastasizing and/or invasive processes (Boyd, D., Cancer Metastasis Rev. (1996) 15(1):77-89; Yokota, J., Carcinogenesis (2000) 21(3):497-503); genes of proteases as well as of molecules that regulate apoptosis and the cell cycle (Matrisian, L. M., Curr. Biol. (1999) 9(20):R776-8; Krepela, E., Neoplasma (2001) 48(5):332-49; Basbaum and Werb, Curr. Opin. Cell Biol. (1996) 8:731-738; Birkedal-Hansen, et al., Crit. Rev. Oral Biol. Med. (1993) 4:197-250; Mignatti and Rifkin, Physiol. Rev. (1993) 73:161-195; Stetler-Stevenson, et al., Annu. Rev. Cell Biol. (1993) 9:541-573; Brinkerhoff, E., and L. M. Matrisan, Nature Reviews (2002) 3:207-214; Strasser, A., et al., Annu. Rev. Biochem. (2000) 69:217-45; Chao, D. T. and S. J. Korsmeyer, Annu. Rev. Immunol. (1998) 16:395-419; Mullauer, L., et al., Mutat. Res. (2001) 488(3):211-31; Fotedar, R., et al., Prog. Cell Cycle Res. (1996) 2:147-63; Reed, J. C., Am. J. Pathol. (2000) 157(5): 1415-30; D'Ari, R., Bioassays (2001) 23(7):563-5); genes that express the EGF receptor; Mendelsohn, J. and J. Baselga, Oncogene (2000) 19(56):6550-65; Normanno, N., et al., Front. Biosci. (2001) 6:D685-707); and the multi-drug resistance 1 gene, MDR1 gene (Childs, S., and V. Ling, Imp. Adv. Oncol. (1994) 21-36).

EXAMPLES

Example 1

Graft Copolymers with Poly(Propyl Acrylic Acid) Backbone for Antisense Delivery

Materials:

Poly(α-propylacrylic acid) and poly(acrylic acid) were purchased from Polymer Source. Poly(ethylene glycol) monomethyl ether MW=2000 was purchased from Aldrich. Poly(ethylene glycol) monomethyl ether MW=5000 was purchased from Fluka. 1-(3-dimethylaminopropyl)-3-ethyl-carbodiimide was purchased from Kawaguchi Chemical Industry Co., Ltd. Tokyo, JAPAN. 4-(dimethylamino)pyridinium 4-toluenesulfonate was synthesized following literature procedures. 1-hydroxybenzotriazole was purchased from Aldrich. All reagents were used as received.

Synthesis of Poly(Acrylic Acid)-Graft-5% Poly(Ethylene Glycol) Monomethyl Ether Copolymer.

Figure 2A:
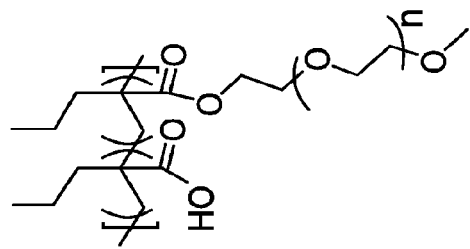
FIGS. 2a and 2b present reaction schemes for synthesizing grafted polymers.
Figure 2A:

Reaction scheme for synthesizing this polymer is presented in FIG. 2a. Poly(acrylic acid) (PAA) (0.1 g, 1.38 mmol repeat units), poly(ethylene glycol) monomethyl ether (mPEG2000) (MW=2000, 140 mg, 70 μmol), 4-(dimethylamino)pyridinium 4-toluenesulfonate (DPTs) (30 mg, 102 μmol), and 5 mL dimethylsulfoxide were charged into a 10 mL round bottom flask with a magnetic stir bar. The mixture was stirred for 30 min until the reagents dissolved. Next, 1-(3-dimethylaminopropyl)-3-ethyl-carbodiimide (EDCI) (133 mg, 694 μmol) was charged into the reaction. The reaction was stirred for 3 weeks, 2 days at room temperature. EDCI (100 mg, 522 μmol) was added on days 4, 9, and 11. The reaction was transferred to a Slide-A-Lyzer cassette with 10,000 MWCO and dialyzed against deionized water for 3 weeks, exchanging water 2-3 times per day except on weekends (6 days) to remove urea side product, DPTs catalyst, and any unreacted mPEG2000. The dialyzed solution was transferred to a 15 mL centrifuge tube, frozen on dry ice, and lyophilized for 1 week. (Yield: 33%) $^1$H NMR (DMSO-$d_6$) δ1.07 (s), 2.28 (br, CH), 3.23 (s, OCH$_3$), 3.32 (t), 3.53 (s, —OCH$_2$CH$_2$O—), 3.67 (t), 3.99 (s), 4.18 (s, C(O)OCH$_2$CH$_2$OPEG), 4.65 (s), 4.68 (br).

Synthesis of Poly(α-Propylacrylic Acid)-Graft-1% Poly(Ethylene Glycol) Monomethyl Ether Copolymer.

Figure 2B:
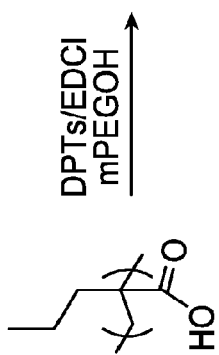
Figure 2B:
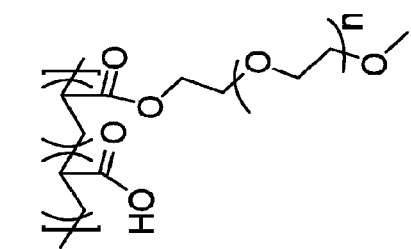
Figure 2B:
Figure 2B:
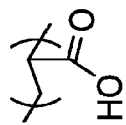
Figure 2B:
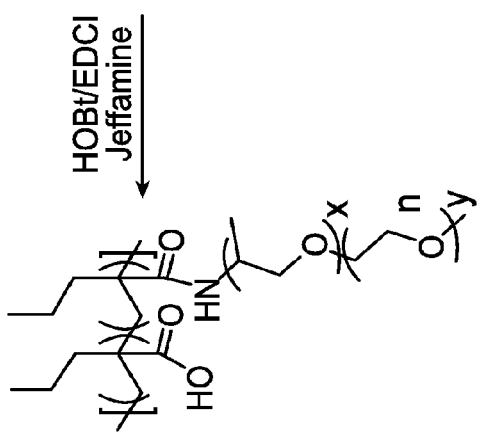
Figure 3A:
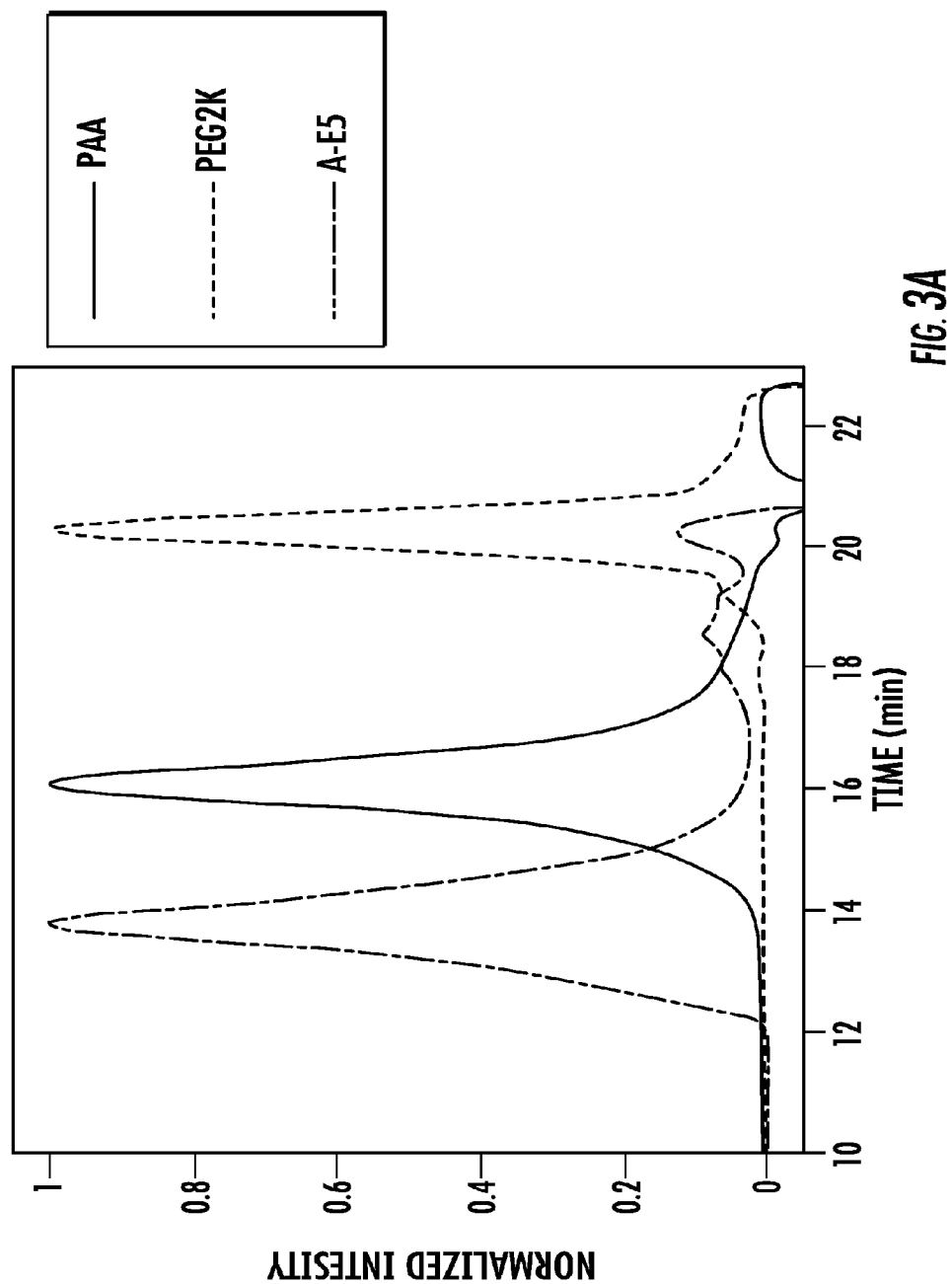
FIG. 3a presents GPC chromatograms for grafting reaction of poly(acrylic acid) with mPEG2000.
Figure 3B:
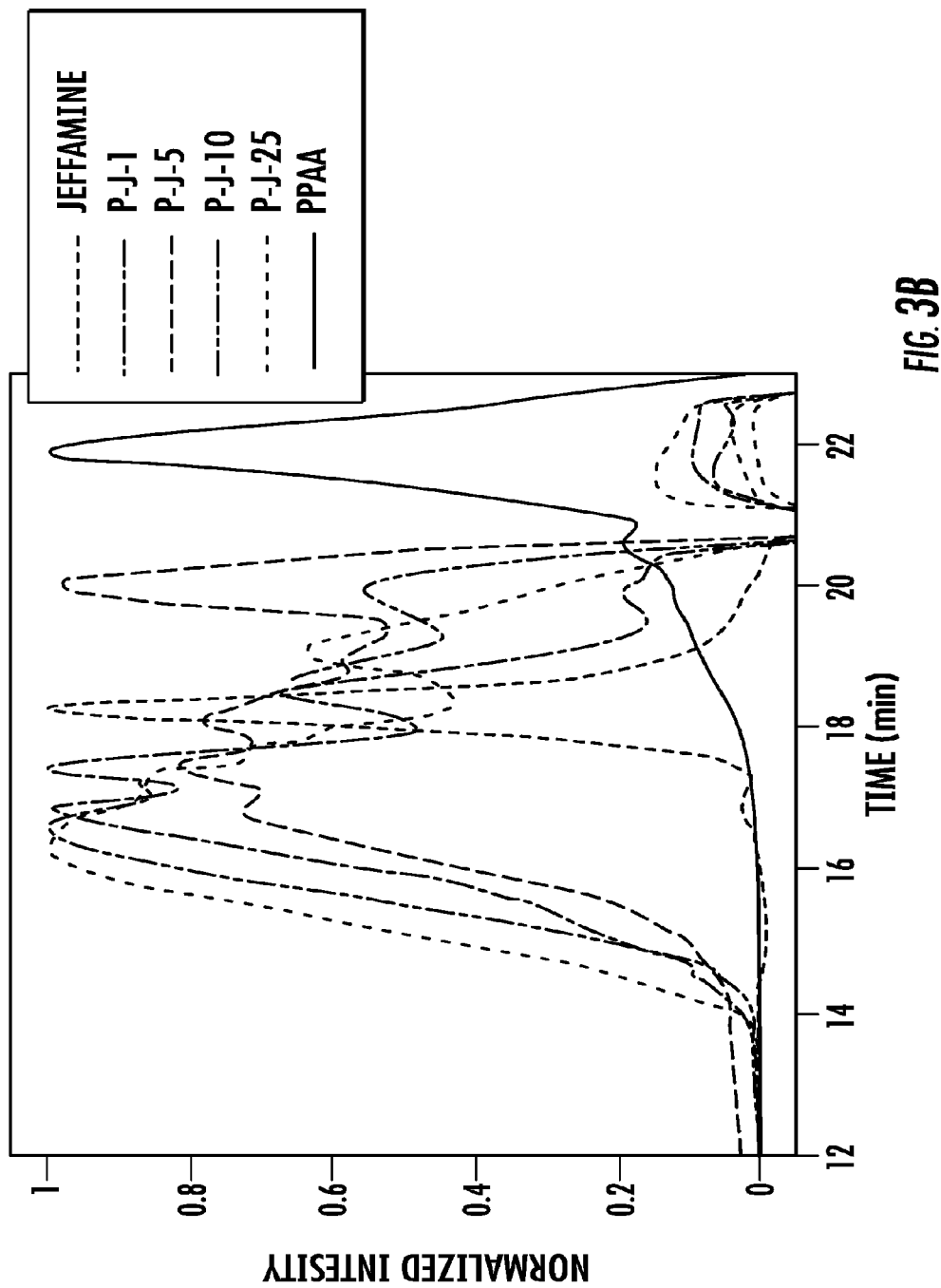
FIG. 3b presents GPC chromatograms for grafting reaction of poly(α-propyl acrylic acid) with Jeffamine.
Figure 3C:
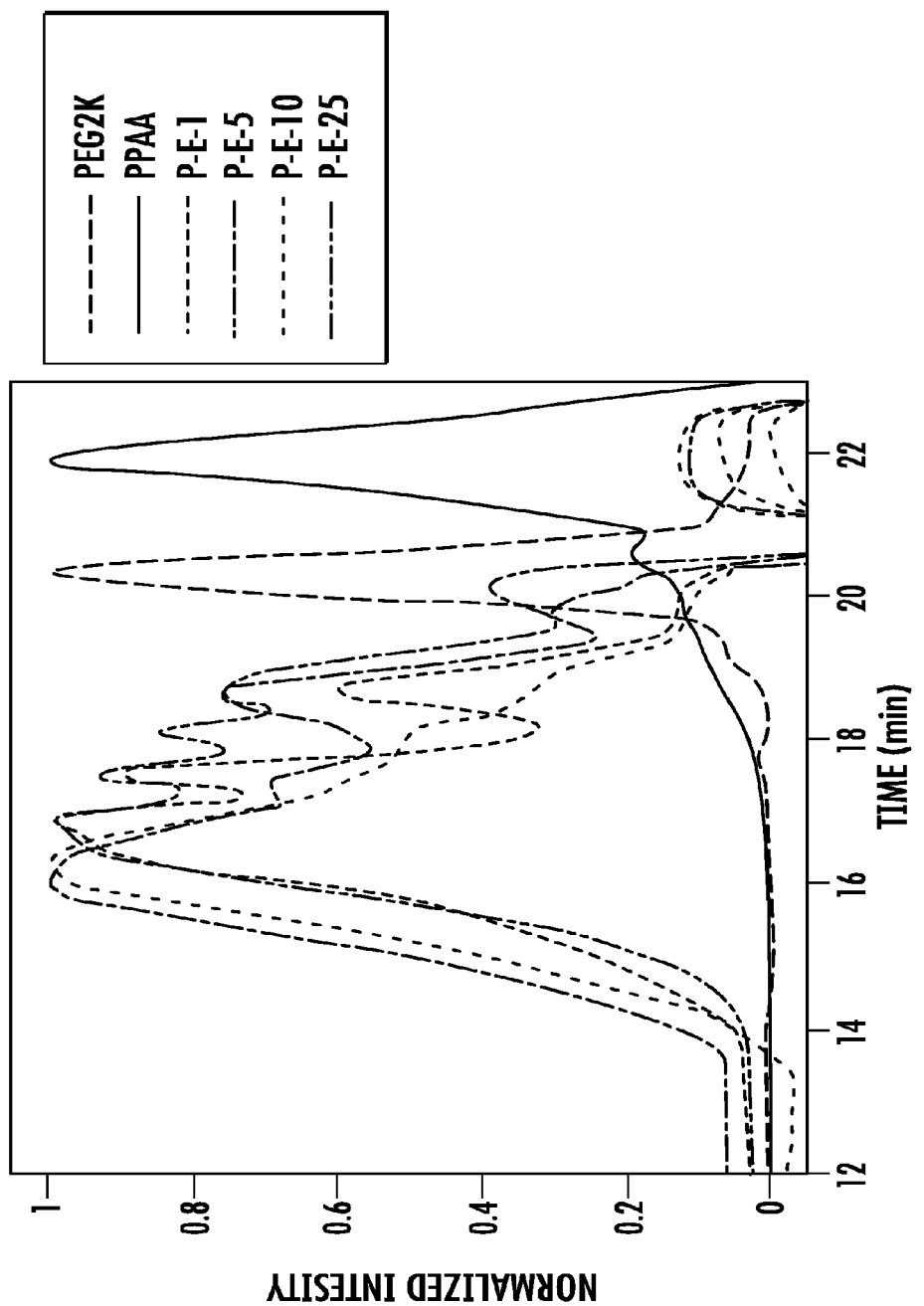
FIG. 3c presents GPC chromatograms for grafting reaction of poly(α-propyl acrylic acid) with mPEG2000.
Figure 3D:
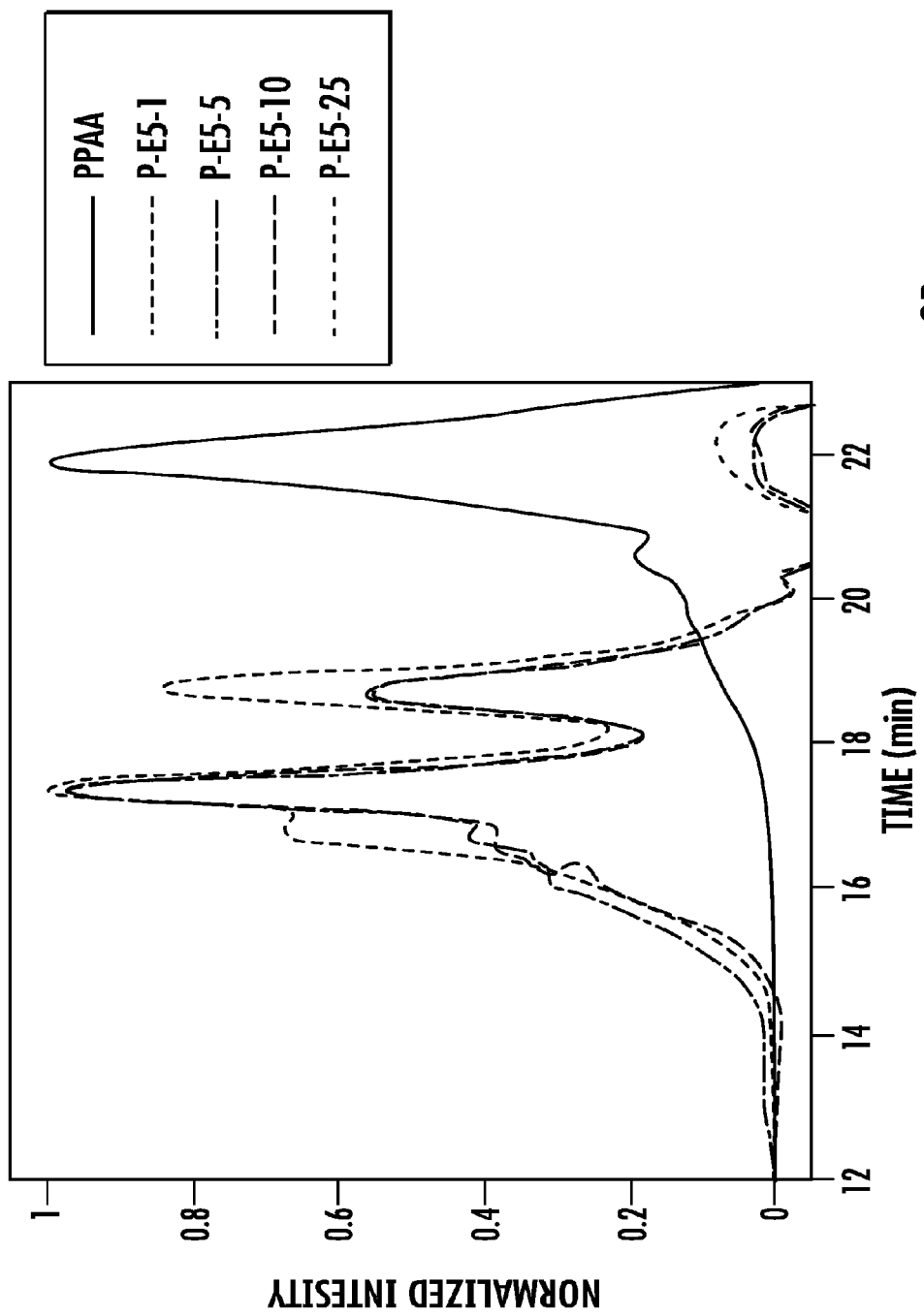
FIG. 3d presents GPC chromatograms for grafting reaction of poly(α-propyl acrylic acid) with mPEG5000.

Reaction scheme for synthesizing this polymer is presented in FIG. 2b. Poly(α-propylacrylic acid) (PPAA) (0.2 g, 174 mmol repeat units), poly(ethylene glycol) monomethyl ether (mPEG2000) (MW=2000, 36 mg, 18 μmol), 4-(dimethylamino)pyridinium 4-toluenesulfonate (DPTs) (11 mg, 37 μmol), and 5 mL dimethylsulfoxide were charged into a 10 mL round bottom flask with a magnetic stir bar. The mixture was stirred for 30 min until the reagents dissolved. Next, 1-(3-dimethylaminopropyl)-3-ethyl-carbodiimide (EDCI) (41 mg, 214 μmol) was charged into the reaction. The reaction was stirred for 3 weeks, 2 days at room temperature. EDCI (100 mg, 522 μmol) was added on days 4, 9, and 11. The reaction was transferred to a Slide-A-Lyzer cassette with 10,000 MWCO and dialyzed against deionized water for 3 weeks, exchanging water 2-3 times per day except on weekends (6 days) to remove urea side product, DPTs catalyst, and any unreacted mPEG2000. The dialyzed solution was transferred to a 15 mL centrifuge tube, frozen on dry ice, and lyophilized for 1 week. (Yield: 22%) $^1$H NMR (DMSO-$d_6$) δ 0.80 (s, CH$_3$), 0.95-2.0 (m, br, CH$_2$ (PPAA), 2.10 (br), 2.17 (br), 2.29 (br), 2.35, 2.41, 2.64, 2.77, 2.9-3.3 (br), 3.2 (OCH$_3$), 3.29 (t), 3.47 (s, —OCH$_2$CH$_2$O—), 3.65 (t), 4.10 (br, C(O)OCH$_2$CH$_2$OPEG), 4.6-4.8 (br), 4.9-5.2 (br), 7.05 (br), 8.45 (br).

Synthesis of Poly(α-Propylacrylic Acid)-Graft-1% Jeffamine Monomethyl Ether Copolymer.

Reaction scheme for synthesizing this polymer is presented in FIG. 2b. Poly(α-propylacrylic acid) (PPAA) (0.2 g, 174 mmol repeat units), Jeffamine monomethyl ether (mJeffamine2000) (MW=2000, 35 mg, 18 μmol), 1-hydroxybenzotriazole (HOBt) (7.5 mg, 56 μmol), and 5 mL dimethylsulfoxide were charged into a 10 mL round bottom flask with a magnetic stir bar. The mixture was stirred for min until the reagents dissolved. Next, 1-(3-dimethylaminopropyl)-3- ethyl-carbodiimide (EDCI) (33 mg, 172 µmol) was charged into the reaction. The reaction was stirred for 3 weeks, 2 days at room temperature. EDCI (100 mg, 522 µmol) was added on days 4, 9, 11. The reaction was transferred to a Slide-A-Lyzer cassette with 10,000 MWCO and dialyzed against deionized water for 3 weeks, exchanging water 2-3 times per day except on weekends (6 days) to remove urea side product and any unreacted mJeffamine. The dialysis medium used on days 11 and 12 was 0.5 M $NaHCO_3$, in order to remove HOBt, the catalyst. The dialyzed solution was transferred to a 15 mL centrifuge tube, frozen on dry ice, and lyophilized for 1 week. (Yield: 9%) $^1$H NMR (DMSO-$d_6$) δ 0.82 (s, $CH_3$), 1.0-2.0 (br, $CH_2$), 2.10, 2.17, 2.2-3.0 (br), 2.9-3.0 (br), 3.2 ($OCH_3$), 3.24-3.42 (m, $CH+CH_2$ (PPO)), 3.47 (s, —$OCH_2CH_2O$—), 3.50, 3.51, 3.52, 3.65 (t), 4.6-4.8 (br), 5.0-5.3 (br), 5.50 (s), 7.08 (d), 7.45-7.60 (br), 7.66 (C(O)NH).

Synthesis of Additional Copolymers.

Slight modifications the synthetic procedures recited in Examples above can be used to generate an array of copolymers as described herein and summarized in Table 1 below.

Graft copolymers can be prepared with mPEG 5000 in similar fashion as those prepared with mPEG 2000 per the protocol recited above (i.e., in Synthesis of PPAA-1 mol % mPEG 2000) with the following modifications. Preparation of copolymers with mPEG 5000 required the addition of methylene chloride to become a homogeneous solution. At the end of the reaction, prior to dialysis, the reaction was concentrated by rotary evaporation to remove methylene chloride. The reaction was stirred at room temperature for 2 weeks, 6 days and dialyzed with three media exchanges per day for 10 days except on the weekend (2 days). Samples were lyophilized for 4 days.

TABLE 1

Summary of Reaction Specifics for Graft Copolymer Synthesis.

| PPAA (g) | Graft | Graft (g) | DPTs (g) | HOBt (g) | EDCI (initial) (g) | EDCI (aliquot size) (g) | Solvent (mL) |
|---|---|---|---|---|---|---|---|
| 0.199 | mPEG2000 | 0.0358 | 0.0109 | — | 0.041 | 0.1 | 5 |
| 0.1983 | mPEG2000 | 0.168 | 0.0388 | — | 0.167 | 0.17 | 5 |
| 0.2009 | mPEG2000 | 0.3513 | 0.081 | — | 0.33 | 0.33 | 5 |
| 0.2018 | mPEG2000 | 0.88 | 0.202 | — | 0.83 | 0.82 | 5 |
| 0.2018 | mPEG5000 | 0.0865 | 0.0116 | — | 0.1 | 0.1 | 5 + 1.5 |
| 0.2015 | mPEG5000 | 0.4346 | 0.0421 | — | 0.16 | 0.2 | 5 + 2.5 |
| 0.203 | mPEG5000 | 0.869 | 0.0819 | — | 0.33 | 0.4 | 8 + 5 |
| 0.203 | mPEG5000 | 2.181 | 0.215 | — | 0.83 | 0.4 | 8 + 8 |
| 0.2006 | mJeff2000 | 0.035 | — | 0.0075 | 0.033 | 0.1 | 5 |
| 0.1901 | mJeff2000 | 0.17 | — | 0.013 | 0.167 | 0.17 | 5 |
| 0.2001 | mJeff2000 | 0.35 | — | 0.03 | 0.33 | 0.33 | 5 |
| 0.1994 | mJeff2000 | 0.88 | — | 0.0758 | 0.83 | 0.82 | 5 |

Graft copolymers can be synthesized with 5 mol % mPEG2000 or mJeffamine2000 in similar fashion as those prepared with 1 mol % of the pendent chains per the respective protocols recited above (i.e., in Synthesis of PPAA-1 mol % mPEG 2000 and Synthesis of PPAA-1 mol % mJeffamine 2000) with the following modifications. Preparation of copolymers with 5 mol % mPEG2000 or mJeffamine2000 required stirring at room temperature for 11 days, with only one portion of EDCI (170 mg) being added after 4 days, and also a final concentration of the preparation in a vacuum oven at 40° C. overnight. The products were redissolved in water for dialysis.

Results:

Polymer Characterization.

NMR spectroscopy was performed on a Varian 400 MHz spectrometer. For $^1$H NMR spectra, d1=1 s with 32-88 scans was used and ca. 10 mg of sample was dissolved in 0.75-1 mL DMSO-$d_6$. Graft copolymers with mPEG5000 were prepared in $CDCl_3$. Molecular weights of the polymers were determined by GPC using Viscotek GPC max VE2001 GPC solvent/sample module, two ViscoGEL™ Columns, and a Viscotek TDA 303 triple detector array. The triple detection consists of a right angle light scattering detector, a differential viscometer, and a differential refractometer that was purchased from Viscotek Corporation (Houston, Tex., USA). The mobile phase used was DMF with 0.1% TFA at 1.0 mL $min^{-1}$. Polymer sample solutions (5 mg $mL^{-1}$, accuracy to 0.001 mg) were filtered through 0.45 µm nylon syringe filters prior to injection. The temperature for the SEC column set and the detector chamber was set at 35° C. Data acquisition and calculation were performed using Viscotek's OmniSEC software, version 4.1. Conventional GPC was used to determine the molecular weights and polydispersity of each of the polymers and to monitor the reaction on a Waters 510 HPLC equipped with a Waters 410 Differential Refractometer, a 5 µm PL gel precolumn, and two PL gel columns (pore size $10^3$-$10^5$ Angstroms), which was calibrated with polystyrene standards using DMF containing 0.1% trifluoroacetic acid at 0.8 mL $min^{-1}$ as the mobile phase.

Percent grafting was calculated by integration of methylene protons of the ester group (C(O)$OCH_2CH_2PEGOCH_3$) relative to the methyl protons of PPAA. The Mark-Houwink parameters were obtained from the Viscotek GPC based on a fit of the data of log intrinsic viscosity vs. log MW. Characterization data are presented in Table 2 below:

TABLE 2

Summary of graft polymer characterization data.

| Target Polymer | Target Graft Density (mol %) | Experimental Graft Density (1H NMR) (mol %) | Mark-Houwink log K | Mark-Houwink a | Mw (kg/mol) | PDI | Quantity (mg) | Expected Yield (100% recovery) (mg) |
|---|---|---|---|---|---|---|---|---|
| poly (propylacrylic acid) | | | −5.734 | 1.28 | 7 | 1.4 | | |

TABLE 2-continued

Summary of graft polymer characterization data.

| Target Polymer | Target Graft Density (mol %) | Experimental Graft Density (1H NMR) (mol %) | Mark-Houwink log K | Mark-Houwink a | Mw (kg/mol) | PDI | Quantity (mg) | Expected Yield (100% recovery) (mg) |
|---|---|---|---|---|---|---|---|---|
| poly (propylacrylic acid)-g-1 mol % PEG2000 | 1 | 4 | −3.479 | 0.594 | 73 | 1.4 | 50 | 230 |
| poly (propylacrylic acid)-g-5 mol % PEG2000 | 5 | 6 | −3.215 | 0.517 | 60 | 1.6 | 50 | 370 |
| poly (propylacrylic acid)-g-10 mol % PEG2000 | 10 | 9 | −3.29 | 0.545 | 94 | 1.4 | 50 | 550 |
| poly (propylacrylic acid)-g-25 mol % PEG2000 | 25 | 12 | −2.56 | 0.362 | 85 | 1.8 | 90 | 1080 |
| poly (propylacrylic acid)-g-1 mol % PEG5000 | 1 | 5 | | | 51 | 1.4 | 250 | 286 |
| poly (propylacrylic acid)-g-5 mol % PEG5000 | 5 | 20 | | | 55 | 1.4 | 220 | 634 |
| poly (propylacrylic acid)-g-10 mol % PEG5000 | 10 | 21 | | | 57 | 1.4 | 320 | 1000 |
| poly (propylacrylic acid)-g-25 mol % PEG5000 | 25 | 35 | | | 55 | 1.5 | 700 | 2380 |
| poly (propylacrylic acid)-g-1 mol % Jeffamine2000 | 1 | 10 | −3.533 | 0.644 | 69 | 1.4 | 20 | 235 |
| poly (propylacrylic acid)-g-5 mol % Jeffamine2000 | 5 | 26 | | | 43 | 1.9 | 30 | 370 |
| poly (propylacrylic acid)-g-10 mol % Jeffamine2000 | 10 | 25 | −3.841 | 0.627 | 58 | 1.9 | 60 | 550 |
| poly (propylacrylic acid)-g-25 mol % Jeffamine2000 | 25 | 38 | −3.073 | 0.478 | 71 | 2.1 | 200 | 1080 |
| poly (acrylic acid) | | | −2.775 | 0.503 | 104 | 1.2 | | |
| poly (acrylic acid)-g-5 mol % PEG2000 | 5 | 3 | −2.624 | 0.472 | 416 | 1.2 | 50 | 250 |

Chromatograms from GPC of the polymers are presented in FIG. 3a-3d.

Graft Polymer Solubility Studies:

The PPAA copolymers of the present invention were assessed for solubility in 10% by volume 1N NaOH (pH 14) or 90% by volume of pH 7.4 phosphate buffer. Results are shown in Table 3 below:

TABLE 3

Summary of Solubility Data

| Molecular Weight | % grafting density | Solubility in Phosphate buffer (pH 7.4) (Did not solubilize in NaOH formulation since ester bonds break, yielding PEG + PPAA) |
|---|---|---|
| PEG 2K-PPAA | 1 | No |
| PEG 2K-PPAA | 5 | No |
| PEG 2K-PPAA | 10 | No |
| PEG 2K-PPAA | 25 | No |
| PEG 5K-PPAA | 1 | No |
| PEG 5K-PPAA | 5 | No |
| PEG 5K-PPAA | 10 | Yes |
| PEG 5K-PPAA | 25 | Yes |

| Molecular Weight | % grafting density | Solubility in NaOH & Phosphate buffer (pH 12:pH 14: pH 7.4 = 2:1:3.67) net pH of solution: 12.5 |
|---|---|---|
| Jeffamine 2K-PPAA | 1 | Yes |
| Jeffamine 2K-PPAA | 5 | Yes |
| Jeffamine 2K-PPAA | 10 | Yes |
| Jeffamine 2K-PPAA | 25 | No |

Figure 4A:
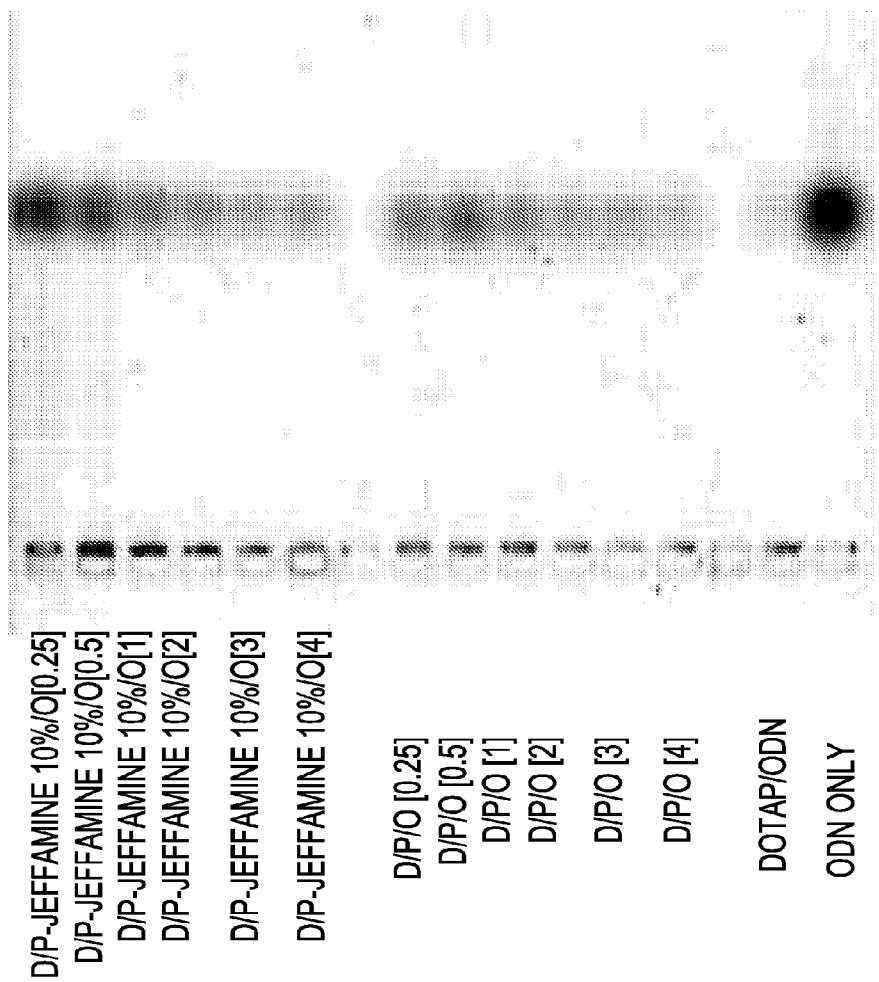
FIGS. 4a and 4b present results of polymer complexation studies.
Figure 4B:
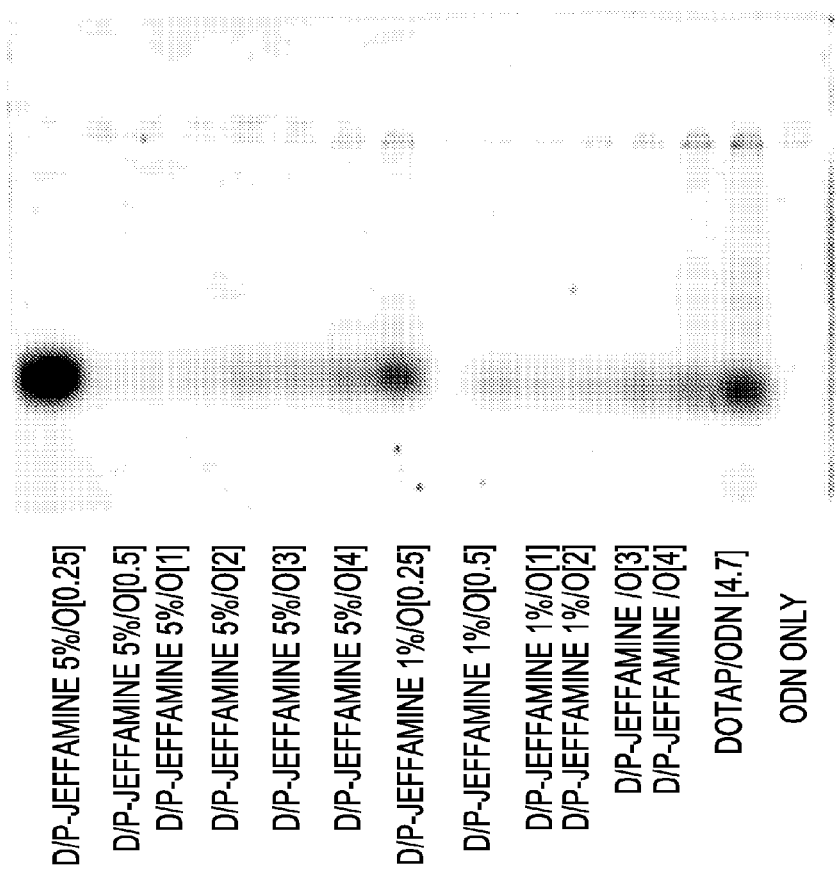

Graft Polymer Complexation Studies:

PPAA-Jeffamine copolymers of various percent grafting density according to the present invention were used to prepare complexes of 1, 2-Dioleoyl-3-Triethylammonium Propane (DOTAP)/PPAA-Jeffamine/Oligodeoxynucleotide (ODN). Results are shown in FIGS. 4a and 4b. As shown in FIG. 4a, addition of PPAA-Jeffamine 2000 10 mol % copolymers to DOTAP/ODN complexes caused higher release of ODN compared to addition of PPAA polymer alone. As shown in FIG. 4b, addition of PPAA-Jeffamine 2000 5 mol % copolymers to DOTAP/ODN complexes caused higher release of ODN compared to addition of PPAA-Jeffamine 2000 1 mol % copolymer.

Figure 5A:
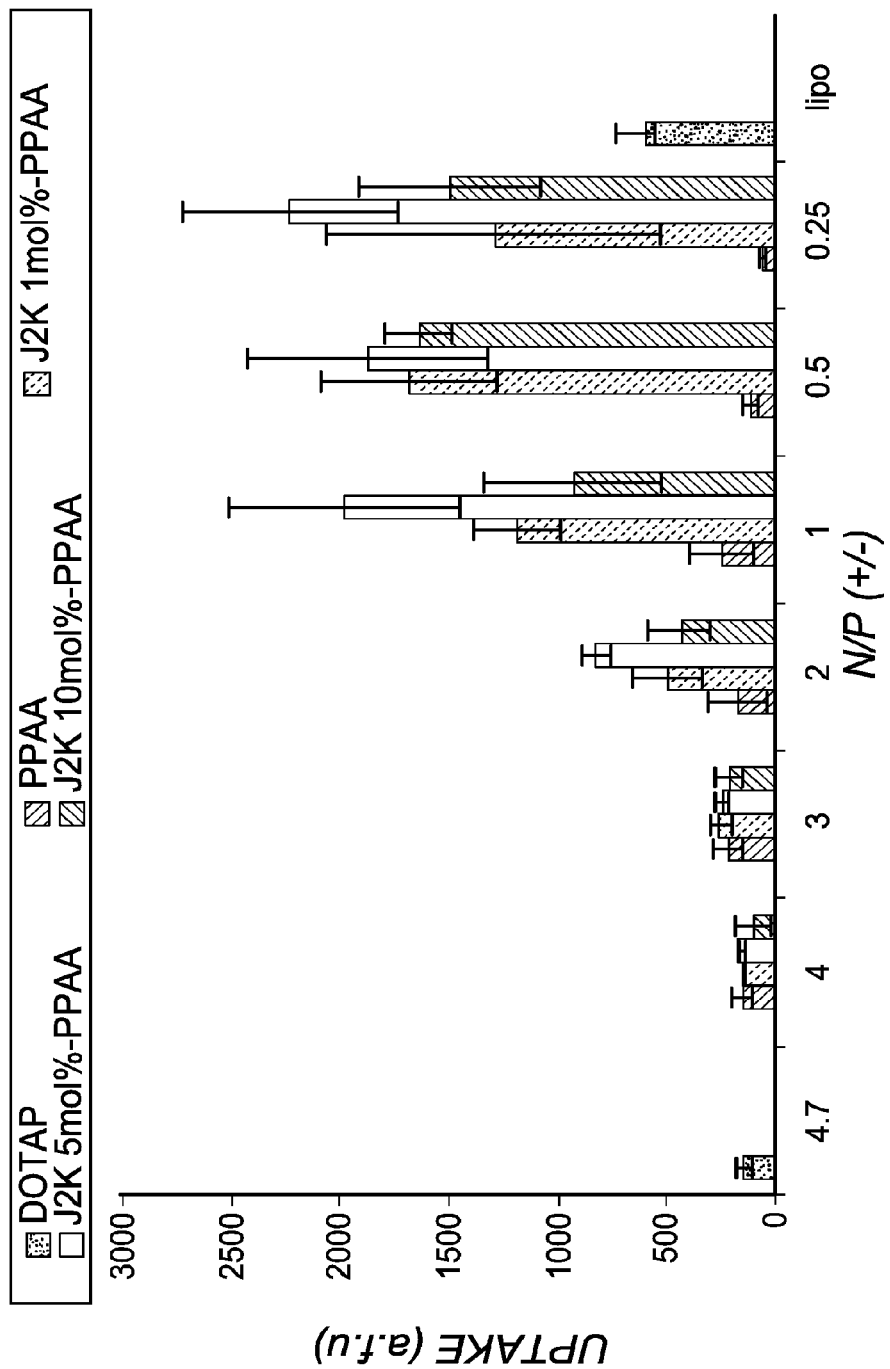
FIGS. 5a and 5b present results of uptake and fluorescence studies, respectively, using PPAA-Jeffamine 2000 (10 mol %) copolymers in DOTAP/ODN complexes.
Figure 5B:
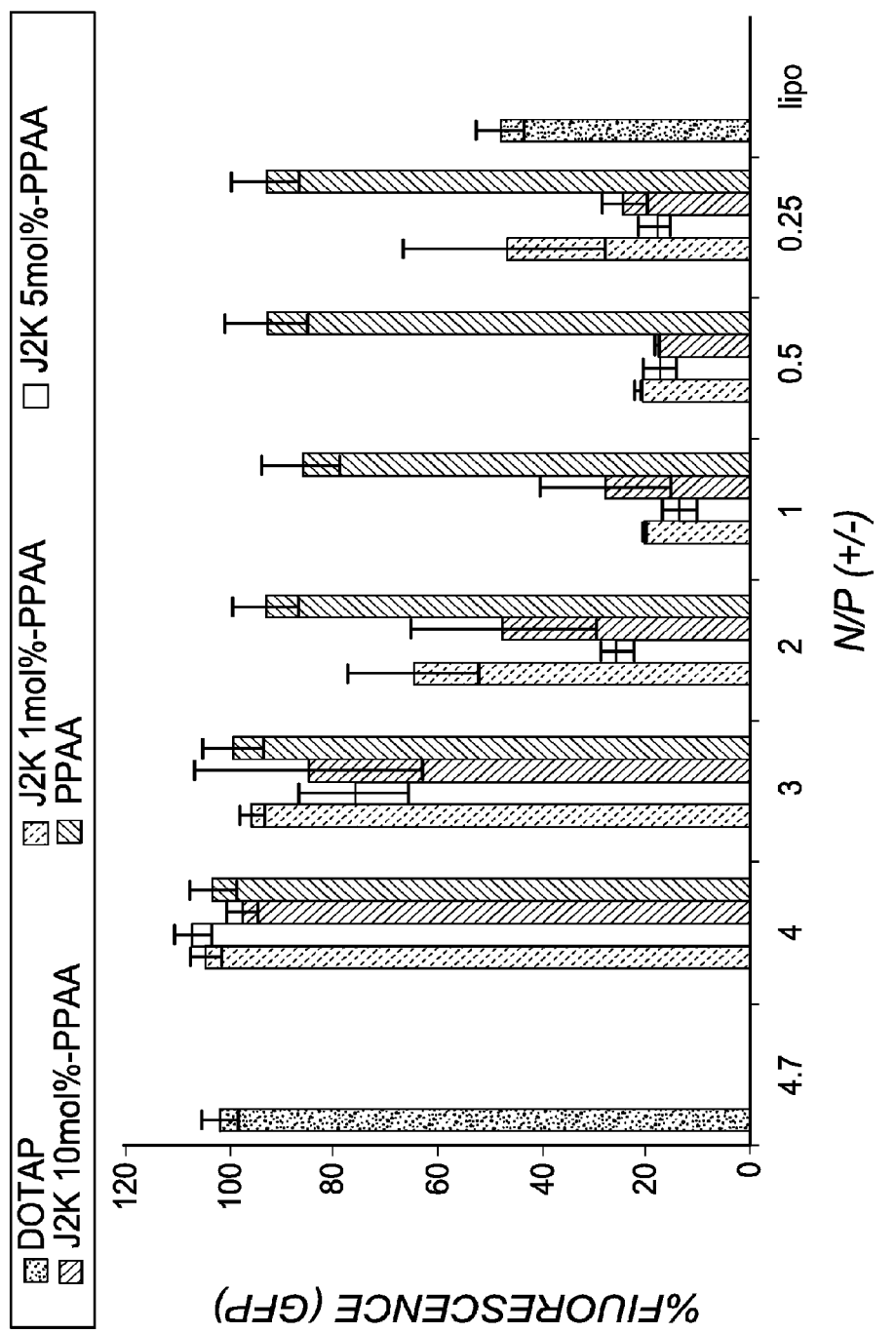
Figure 6A:
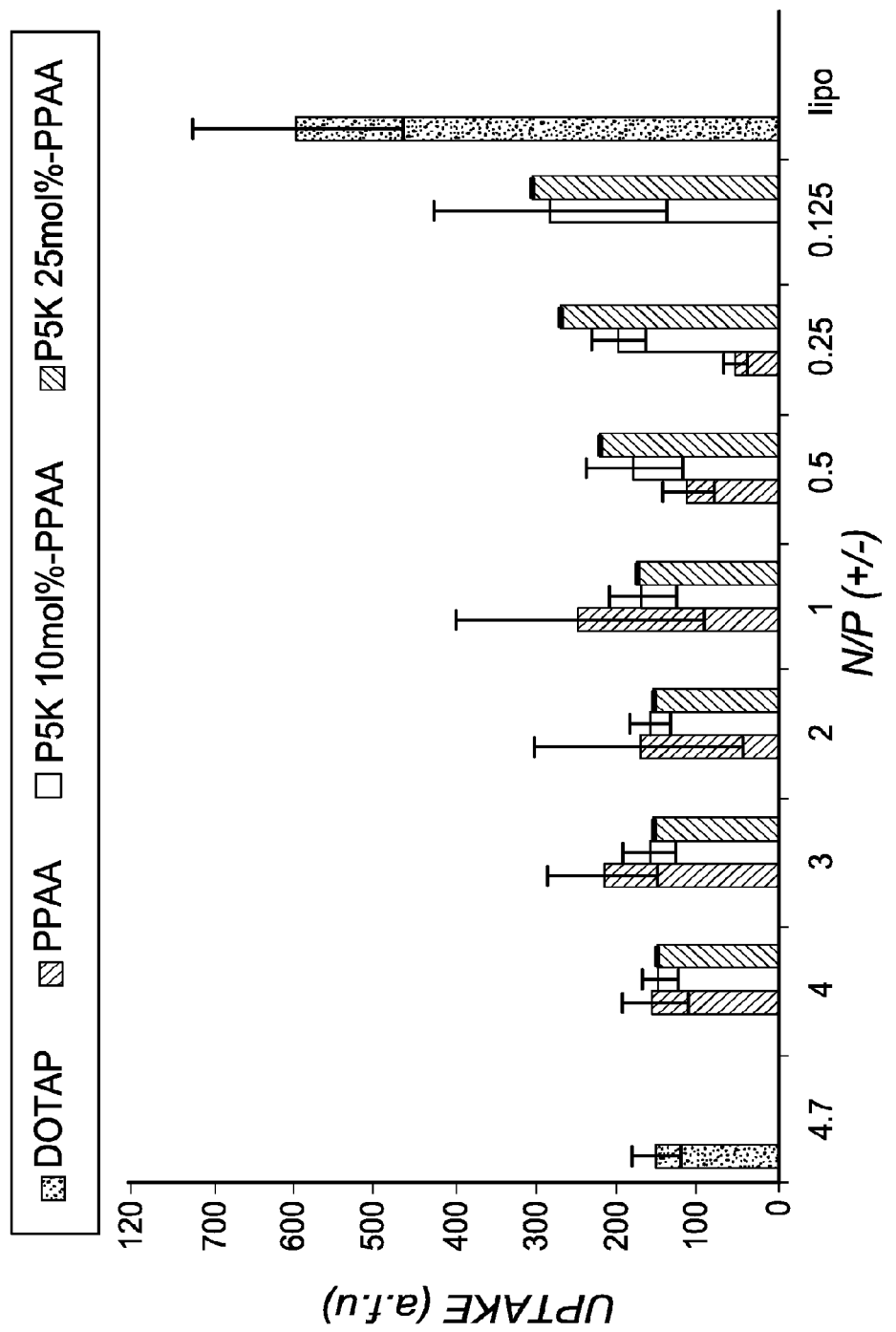
FIGS. 6a and 6b present results of uptake and fluorescence studies, respectively, using PPAA-PEG 5000 (10 mol % or 25 mol %) copolymers in DOTAP/ODN complexes.
Figure 6B:
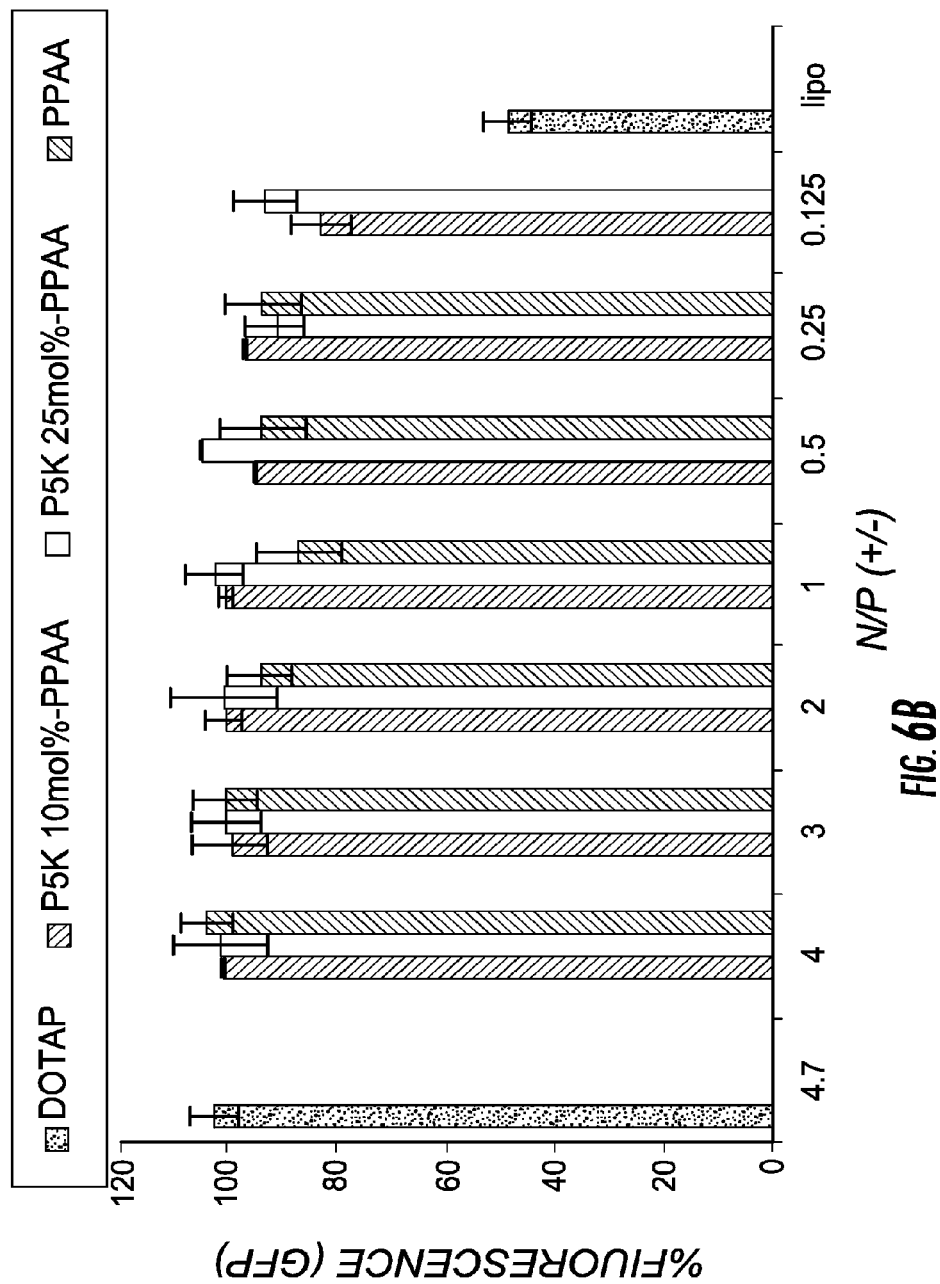

Graft Polymer Uptake and Delivery Studies:

A therapeutic delivery system comprising instant graft copolymers was assessed using Chinese Hamster Ovary (CHO) cells stably expressing Green Fluorescent Protein (GFP). PS ODN 157, an anti-GFP target sequence with a phosphorothioate backbone, was administered in a transfection system of serum-containing media (8% FBS). Uptake (a.f.u.) data shown in FIGS. 5A and 6A is indicative of the levels of fluorescently tagged PS ODN inside the cells, while % Fluorescence (GFP) data shown in FIGS. 5B and 6B is indicative of the GFP fluorescence of 10,000 cells. Analyses were performed at 24 hours post-transfection.

As shown in FIG. 5a, levels of PS-ODN uptake for DOTAP/ODN (N/P=4.7) are very low. The addition of anionic polymer PPAA increases uptake only moderately. However, addition of copolymer PPAA-Jeffamine 2000 10 mol % copolymer significantly increases uptake (10 fold) @ N/P=0.5. As shown in FIG. 5b, no antisense silencing effect is seen with the DOTAP/ODN (N/P=4.7) system. Addition of PPAA polymers reduces GFP expression by only 20% @ N/P=1. However, addition of PPAA-Jeffamine 2000 10 mol % copolymer to DOTAP/ODN reduces GFP expression significantly (~80%). The maximum shut off of expression occurs @ N/P=0.5.

FIG. 6a and FIG. 6b show uptake and percent fluorescence results, respectively, using PPAA-PEG 5000 (10 mol % or 25 mol %) copolymers in DOTAP/ODN complexes. As evident therein, no antisense silencing effect can be seen with the DOTAP/ODN/PPAA-PEG 5000 complexes.

Figure 7A:
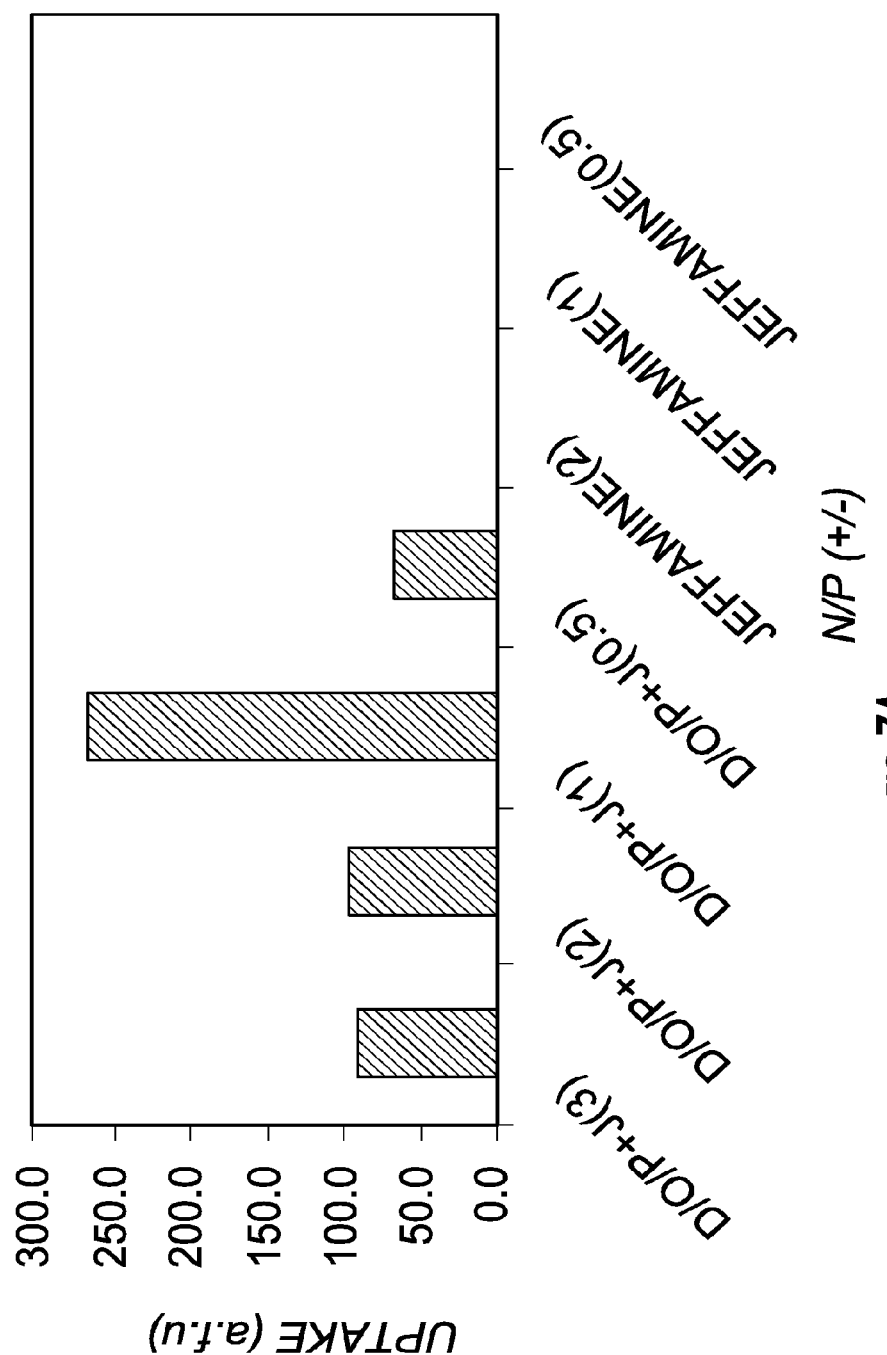
FIGS. 7a and 7b present results of uptake and fluorescence studies, respectively, using PPAA-Jeffamine 2000 (10 mol %) copolymers in DOTAP/ODN complexes.
Figure 7B:
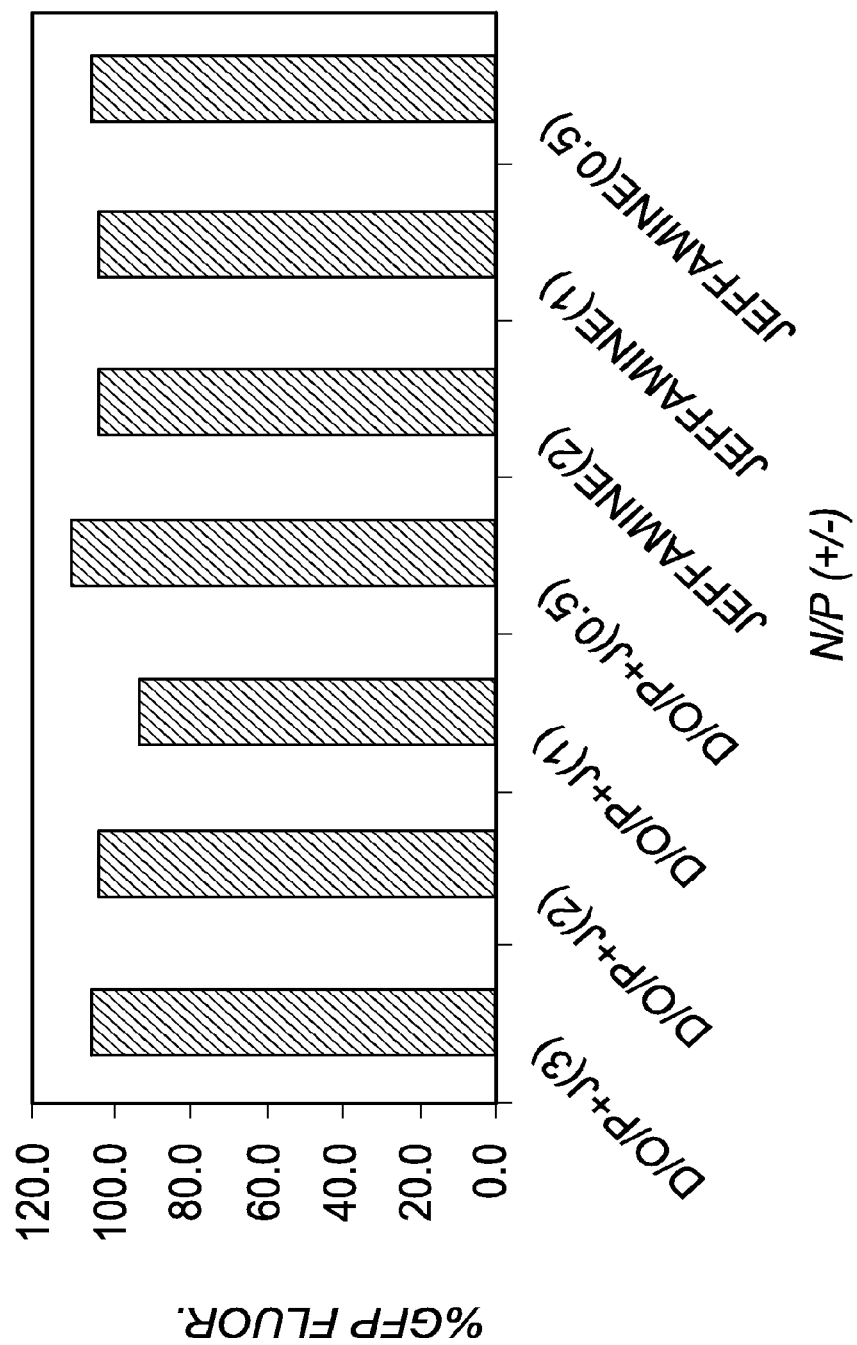

FIG. 7a and FIG. 7b show uptake and percent fluorescence results, respectively, using Jeffamine conjugated to PPAA in DOTAP/ODN complexes. Furthermore, Table 4 summarizes uptake and percent fluorescence results for scrambled ODN and Table 5 presents uptake and percent fluorescence results for grafted polymers DOTAP/ODN.

TABLE 4

Uptake and percent fluorescence results for scrambled ODN.

| | % Green Fluorescence | stdev | uptake of Cy5-ODN | stdev |
|---|---|---|---|---|
| D/O157 (4.7) | 103.0 | 3.4 | 150.1 | 27.4 |
| D/Oscrambled (4.7) | 113.2 | | 128.9 | |
| D/O157/PPAA (1) | 87.1 | 7.8 | 243.4 | 151.8 |
| D/Oscrambled/P (1) | 94.9 | | 436.9 | |
| D/O157/J2K 5 mol %-P (0.5) | 17.5 | 3.2 | 1874.0 | 546.7 |
| D/Osc/J2K 5 mol %-P (0.5) | 123.9 | 22.7 | 1537.2 | 336.0 |
| D/O157/J2K10 mol %-P (0.5) | 18.1 | 0.6 | 1646.1 | 157.3 |
| D/Osc/J2K10 mol %-P (0.5) | 58.3 | | 1544.0 | |

TABLE 5

Uptake and percent fluorescence results for grafted polymers by themselves

| Description | | N/P | % Green Fluorescence | Uptake Cy5-ODN |
|---|---|---|---|---|
| J2K1mol %-P | polymer only | 0.5 | 94.0 | 1.0 |
| J2K5mol %-P | polymer only | 0.5 | 96.0 | 1.0 |
| J2K10mol %-P | polymer only | 0.5 | 94.4 | 1.0 |

As evident therein, it is (DOTAP/ODN/PPAA-Jeffamine) and not Jeffamine polymer (DOTAP/ODN/PPAA+Jeffamine) by itself in the DOTAP/ODN complexes that induces the enhanced antisense effect under serum conditions.

Example 2

Using Graft Copolymers for Delivery of Antisense Oligonucleotides in the Presence of Serum Materials:

A phosphorothioate oligodeoxynucleotide tagged with Cy5 (5'-/5Cy5/TTG TGG CCG TTT ACG TCG CC-3') was used for physical and biological studies. The 20-mer oligonucleotide (ODN) (EGFP157), previously selected for down regulation of d1EGFP, was used to assess the degree of silencing or antisense effect. We have confirmed that the presence of the Cy5 tag does not significantly alter the delivery of ODNs into cells or the ability of ODNs to bind with mRNA and achieve an antisense effect. The ODNs were obtained from Integrated DNA Technologies (Coralville, Iowa) and delivered as HPLC grade. Before use, lyophilized ODNs were resuspended in phosphate buffer saline (PBS) (Invitrogen, Carlsbad, Calif.) solution of pH 7.2 to a concentration of 100 µM.

The cationic liposomal formulation, N-[1-(2,3-dioleyloxyl)propyl]-N,N,N-trimethylammonium methyl sulphate (DOTAP), was purchased from Roche Applied Science (Indianapolis, Ind.) in a liposomal form. Lipofectamine2000 was purchased from Invitrogen and used as directed. Poly (α-propylacrylic acid) (PPAA) (Mn=27 kDa) was purchased from Polymer Source (Montreal, Canada). PEO monomethyl ether (MW=5 kDa) was purchased from Fluka. 1-(3-dimethylaminopropyl)-3-ethyl-carbodiimide was purchased from Kawaguchi Chemical Industry Co., Ltd. (Tokyo, Japan). 4-(dimethyl-amino) pyridinium 4-toluenesulfonate was synthesized following a published procedure. Jeffamine M-2070 (MW=2 kDa, EO/PO=31/10) was a gift from Huntsman International, LLC (Woodlands, Tex.).

For characterization studies, PPAA polymer, which was received as a dried powder, was solubilized in 0.1 N NaOH in PBS (pH 13). The Jeffamine M-2070 grafted PPAA copolymer (PPAA-g-Jeffamine) was solubilized in a NaOH-PBS (pH 12.5) formulation and then diluted. The PEO grafted PPAA copolymer (PPAA-g-PEO) was solubilized in PBS (pH 7.4). Solutions of DOTAP, ODN and polymers were stored at 4° C. and vortexed prior to use. All other reagents and solvents were purchased from Sigma-Aldrich (St. Louis, Mo.), unless noted otherwise. All buffers were prepared in MilliQ ultrapure water and filtered (0.22 µm) prior to use.

Synthesis of Graft Copolymers

Methods described in Moore, J., Stupp, S I. *Journal of Organic Chemistry* 1990, 55, 3374 and Hourdet D, L. A. F., Audebert R. *Polymer* 1997, 38, 2535-2547 were followed.

For the PPAA-g-PEO copolymer, 200 mg PPAA was added to 5 mL DMSO along with 11 mg DPTS, and a slight molar excess of PEO monomethyl ether required to achieve the target graft ratio. The mixture was stirred for 30 min at room temperature, after which 41 mg EDCI was added. The reaction was allowed to proceed at room temperature and driven to completion with subsequent 100 mg aliquots of EDCI added on days 4, 9, and 11. The reaction mixture was then transferred to a Slide-A-Lyzer cassette with 10 kDa cut off and exhaustively dialyzed against deionized water. The dialyzed solution was then lyophilized.

For the PPAA-g-Jeffamine copolymer, the same synthesis, dialysis and lyophilization protocols that were used for PPAA-g-PEO copolymer were followed, with the exception that Jeffamine M-2070 replaced the PEO monomethyl ether and HOBt was used as the catalyst in place of DPTS.

Conventional gel permeation chromatography was used to monitor the progress of the reactions and as an indicator of the final molecular weight and polydispersity of the graft copolymers. This was performed with the Waters 510 HPLC unit equipped with a Waters 410 Differential Refractometer, a 5 µm PL gel precolumn, and two PL gel columns (pore size $10^3$-$10^5$ Angstroms) that have been calibrated with polystyrene standards by using DMF containing 0.1% trifluoroacetic acid as the mobile phase at a flow rate of 0.8 mL $min^{-1}$.

Delivery Complex Preparation:

The delivery complexes are self-assembled from their components through electrostatic interactions, first between the cationic DOTAP liposomes and anionic ODN, and then between the DOTAP/ODN complexes and the anionic polyelectrolytes (PPAA, PPAA-g-PEO or PPAA-g-Jeffamine). Complexes were prepared using a DOTAP/ODN weight ratio of 10:1, which corresponds to a charge ratio of 4.7 (+/−). The calculated net charge ratio is defined as the ratio of the moles of DOTAP amine groups to the sum of the moles of ODN phosphate groups and PPAA carboxylic acid groups. The DOTAP working concentration used was 20 µg/ml (as recommended by Roche). For the ODN encapsulation assay, complexes were formed in PBS to yield a final ODN concentration of 750 nM. For gene silencing experiments, complexes were formed in PBS to yield a final ODN concentration of 300 nM. All DOTAP/ODN/polyelectrolyte complexes were formed by mixing equal volumes of DOTAP and ODN, followed by incubation for minutes at room temperature. Polyelectrolyte was then added to the DOTAP/ODN solution to produce the desired charge ratio. DOTAP and ODN were assumed to be completely ionized (100%), while the carboxylic acids of PPAA were assumed to be 33% ionized at pH 7.4 based on its pKa value. This assumption made for PPAA was also applied to the remaining PPAA groups in PPAA-g-PEO and PPAA-g-Jeffamine copolymers. LipofectAMINE 2000 (Invitrogen, Carlsbad, Calif.) complexed to ODN in a weight ratio of 2:1 was employed as a control. The ratio of complex volume to buffer/media volume was maintained constant at 1:4.

Cell Culture.

The preparation of Chinese hamster ovary (CHO-K1) cells stably integrated with destabilized EGFP (d1EGFP) transgene has been described previously[14,20]. A glioblastoma (U87) cell line (ATCC, Manassas, Va.) also expressing d1EGFP was developed in a similar manner by transfecting these cells with the 4.9-kb pd1EGFP-N1 plasmid (BD Biosciences Clontech, Palo Alto, Calif., USA), followed by clonal selection and maintenance under selective pressure of G418 (Invitrogen, Carlsbad, Calif.). The CHO-d1EGFP cell line was maintained in F-12K medium (Kaighn's modification of Ham's F-12; ATCC, Manassas, Va.) supplemented with 10% fetal bovine serum (FBS) (Invitrogen, Carlsbad, Calif.), 100 U/mL penicillin (Invitrogen, Carlsbad, Calif.) and 100 µg/mL streptomycin (Invitrogen, Carlsbad, Calif.). The U87-d1EGFP cell line was maintained in 10% Minimal Essential Media (MEM) (ATCC, Manassas, Va.) supplemented with 10% FBS, 4 mM L-glutamine (Invitrogen, Carlsbad, Calif.), 1 mM sodium pyruvate, 1 mM non-essential amino acids, 100 U/mL penicillin and 100 µg/mL streptomycin. Both cell types were maintained under constant selective pressure by using G418 antibiotic (500 µg/ml). Cells were cultivated in a humidified atmosphere at 5% $CO_2$ and 37° C.

Results

Characterization of PPAA-g-PEO and PPAA-g-Jeffamine:

The extent of PEO and Jeffamine M-2070 grafting onto PPAA backbones was determined by NMR spectroscopy, which was performed on a Varian 400 MHz spectrometer. The percentage of grafting was calculated by the ratio of the integrated peak areas of the methylene protons in the grafted chains to the methyl protons in PPAA. For the PPAA-g-PEO, $^1$H NMR (DMSO-$d_6$) δ 0.80 (s, $CH_3$), 0.95-2.0 (m, br, $CH_2$(PPAA), 2.10 (br), 2.17 (br), 2.29 (br), 2.35, 2.41, 2.64, 2.77, 2.9-3.3 (br), 3.2 ($OCH_3$), 3.29 (t), 3.47 (s, —$OCH_2CH_2O$—), 3.65 (t), 4.10 (br, C(O) $OCH_2CH_2OPEO$), 4.6-4.8 (br), 4.9-5.2 (br), 7.05 (br), 8.45 (br). For the PPAA-g-Jeffamine, $^1$H NMR (DMSO-$d_6$) δ 0.82 (s, $CH_3$), 1.0-2.0 (br, $CH_2$), 2.10, 2.17, 2.2-3.0 (br), 2.9-3.0 (br), 3.2 ($OCH_3$), 3.24-3.42 (m, CH+$CH_2$ (PPO), 3.47 (s, —$OCH_2CH_2O$—), 3.50, 3.51, 3.52, 3.65 (t), 4.6-4.8 (br), 5.0-5.3 (br), 5.50 (s), 7.08 (d), 7.45-7.60 (br), 7.66 (C(O)NH).

The NMR spectra of PPAA-g-PEO copolymer contain chemical shifts expected for methylene protons of the PEO ester moiety formed by reaction of the PPAA carboxylic acids with the primary alcohol of PEO (4.1 ppm). In the case of PPAA-g-Jeffamine, the spectra contain the amide proton (NH) that is formed by reaction of PPAA carboxylic acid groups with the primary amine of Jeffamine (7.6 ppm). The GPC chromatograms of the isolated products also reveal the disappearance of the starting materials and the appearance of new multimodal peaks at high molecular weight.

Because only a few of the graft copolymers from the initial set synthesized are soluble in aqueous buffer, even when NaOH base is added to enhance solubility, the physical and biological studies presented here are limited to investigations of two similar graft copolymers: 1) PPAA-g-PEO containing 21 mole % grafting of the 5 kDa PEO monomethyl ether, total number-average molecular weight of 57 kDa, and polydispersity index of 1.4; and, 2) PPAA-g-Jeffamine containing 25 mole % grafting of the 2 kDa Jeffamine M-2070, total number-average molecular weight of 58 kDa, and polydispersity index of 1.9. These graft copolymers are not completely analogous, as the pendent comb chains of PEO are of greater molecular weight than the pendent Jeffamine chains. Nevertheless, these two graft copolymers provide us with sufficient structural similarities to allow comparisons of their abilities to deliver ODN to cells in the presence of serum-containing treatment conditions.

Physical Characteristics of DOTAP/Polymer/ODN Complexes:

The degree of ODN encapsulation in the vectors was determined by measuring the quenching of fluorescence from Cy5 labeled ODNs (F-ODNs). Solutions of DOTAP/ F-ODN in the presence and absence of PPAA or PPAA graft copolymers were loaded into a polystyrene clear bottom 96-well black plate (Corning, Corning, N.Y.). The Cy5 fluorescence intensity was measured at excitation and emission wavelengths of 630 and 680 nm, respectively, using an Ascent Fluorescence Multi-well Plate Reader. After background subtraction each data point was normalized to control, i.e., uncomplexed ODN. Disruption of the complexes to recover encapsulated F-ODN was achieved by using a 0.25% solution of Triton X-100. Negligible fluorescence (close to background) was obtained for carrier (in the absence of ODN) and Triton X-100 (in the absence of ODN). The degree of encapsulation in the presence and absence of Triton X-100 was calculated by the following formula:

$$\% \text{ Encapsulation} = \frac{(F_{680,sample} - F_{680,PBS})}{(F_{680,ODN} - F_{680,PBS})} * 100$$

Figure 8:
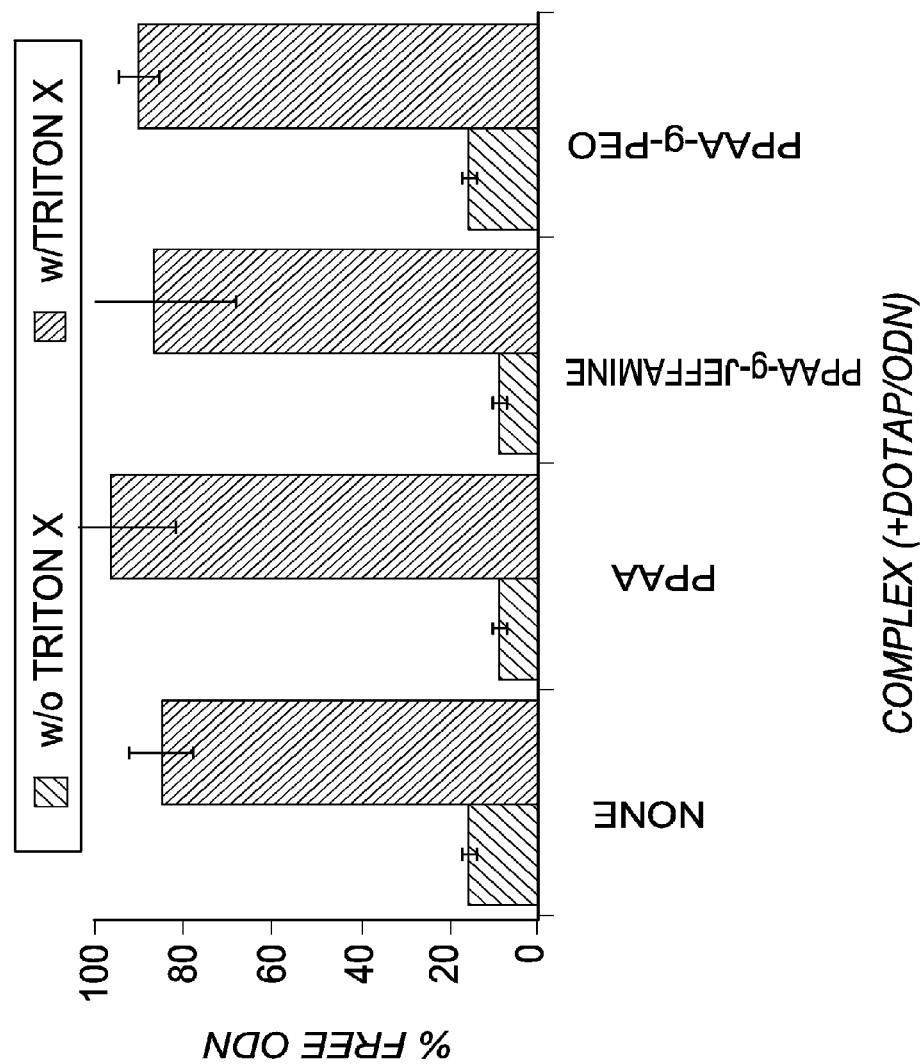
FIG. 8 presents results of studies on degree of ODN encapsulation by DOTAP/ODN complexes containing polyelectrolytes PPAA, PPAA-g-Jeffamine or PPAA-g-PEO.

In this binding study, the charge ratio of DOTAP/ODN is fixed at 4.7 (corresponding to a weight ratio of 10/1), and the net charge ratio of complexes containing anionic PPAA or graft copolymers is 1.0. The degree of ODN binding in the various complexes is quite similar, with less than 20% free ODN detected either in the presence or absence of polymer. Further, the encapsulated ODN is recovered when the complexes are disrupted with Triton X-100 surfactant, s shown in FIG. 8. Fluorescence (Cy5) corresponds to free Cy5-ODN in solution, while absence of fluorescence indicates quenching or ODN in bound (complexed) state. These results demonstrate that the binding ability of the cationic liposome, DOTAP, with anionic ODN is unaltered by the addition of PPAA or graft copolymers, and furthermore that the ODN is still part of the complexes and can be recovered.

Figure 9:
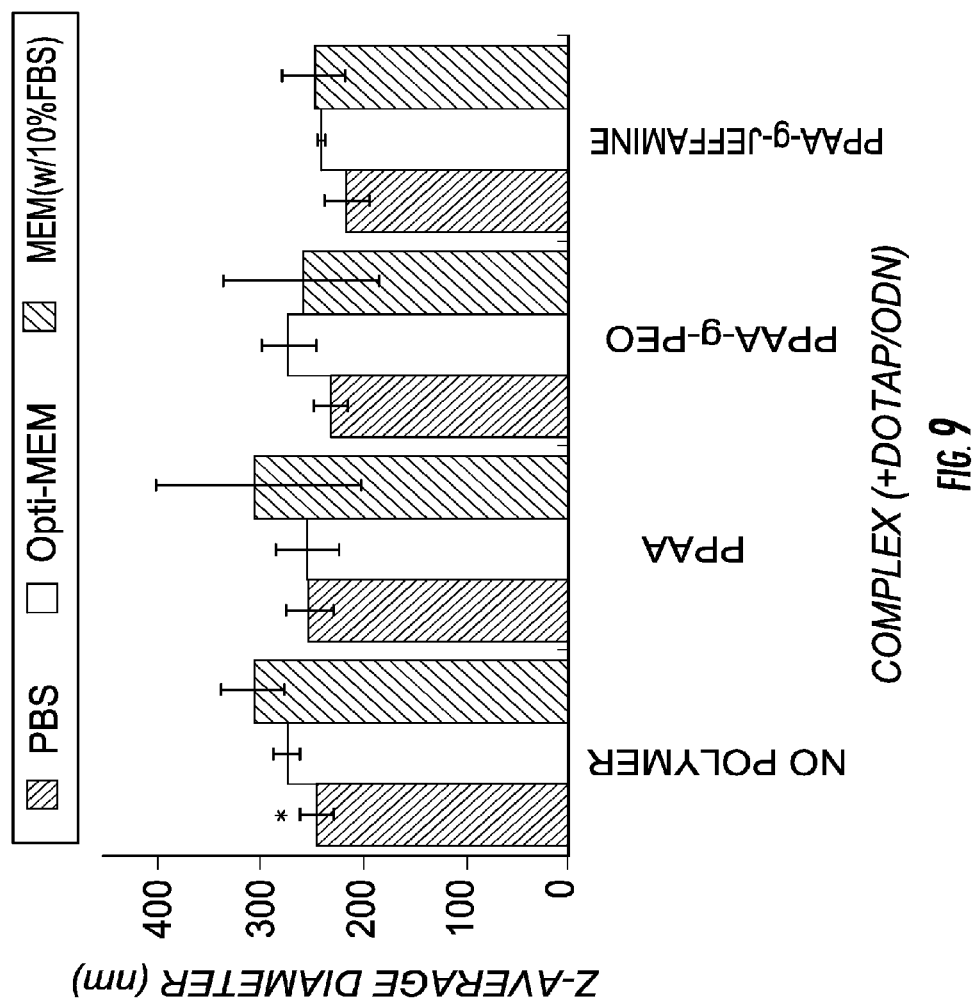
FIG. 9 presents results of studies on mean hydrodynamic diameter (nm) of DOTAP/ODN complexes in the presence of PPAA, PPAA-g-PEO or PPAA-g-Jeffamine.

To further characterize the complexes, particles were examined using dynamic light scattering. Particles sizes were measured at a DOTAP/ODN charge ratio of 4.7 and a DOTAP/ODN/polyelectrolyte net charge ratio of 1 in PBS, Opti-MEM (serum-free media) and MEM (containing 10% FBS). The particle sizes of DOTAP/ODN complexes in the absence of polymer were smallest in PBS solution, compared to opti-MEM or MEM with 10% FBS. The particle sizes of all the other complexes containing PPAA, PPAA-g-PEO or PPAA-g-Jeffamine were found to be independent of the buffer solution. In general, all of the complexes form fairly stable particles in the three buffer solutions with sizes ranging from 215-300 nm, as shown in FIG. 9. In FIG. 9, data represent mean±SD (n=3) and asterisk represents statistical significance (p<0.05) vs. the other media within a formulation. Overall, these observations are in agreement with the results from the ODN encapsulation studies, where all the complexes bind to ODN equally efficiently. Further, they indicate that neither PPAA nor its graft copolymers induces widespread aggregate formation, despite the overall charge neutrality of the system.

Hemolysis

The membrane-disruptive activity of PPAA and the grafted polymers was assessed using a hemolysis assay as described in Murthy, N.; Robichaud, J. R.; Tirrell, D. A.; Stayton, P. S.; Hoffman, A. S. *J Control Release* 1999, 61, 137-143. Stock solutions of polymers were vortexed thoroughly to ensure complete solubility, and dilutions of the polymer were prepared fresh. Phosphate buffers, in the pH range 5.5-7.0, and citrate buffer of pH 5.0, were prepared by titration of 100 mM sodium mono and diphosphate and 100 mM sodium citrate, respectively, to achieve the appropriate pH values. Solutions of PPAA, PPAA-g-PEO and PPAA-g-Jeffamine were added to pH buffers 5.0, 5.5, 6.0, 6.5 and 7.0 at 40, 240 and 400 μg/ml and vortexed thoroughly. To these polymer solutions, fresh RBCs that had been washed just prior three times with 100 mM NaCl were added at $10^8$ cells/ml, incubated in a water bath at 37° C. for 1 hr, and then centrifuged for 4 min and 400 g to pellet the intact RBCs. The absorbance of the supernatants (541 nm) was determined on a UV spectrophotometer (Thermo Spectronic). Experimental controls included RBCs in pH buffers in the absence of polymer (negative control) and RBCs in distilled water (positive control). Each test was performed in triplicate. The percentage of hemolysis was determined using the formula below:

$$\text{Hemolysis} = \frac{(A_{541,sample} - A_{541,buffer})}{(A_{541,distilledwater})} * 100$$

Figure 10:
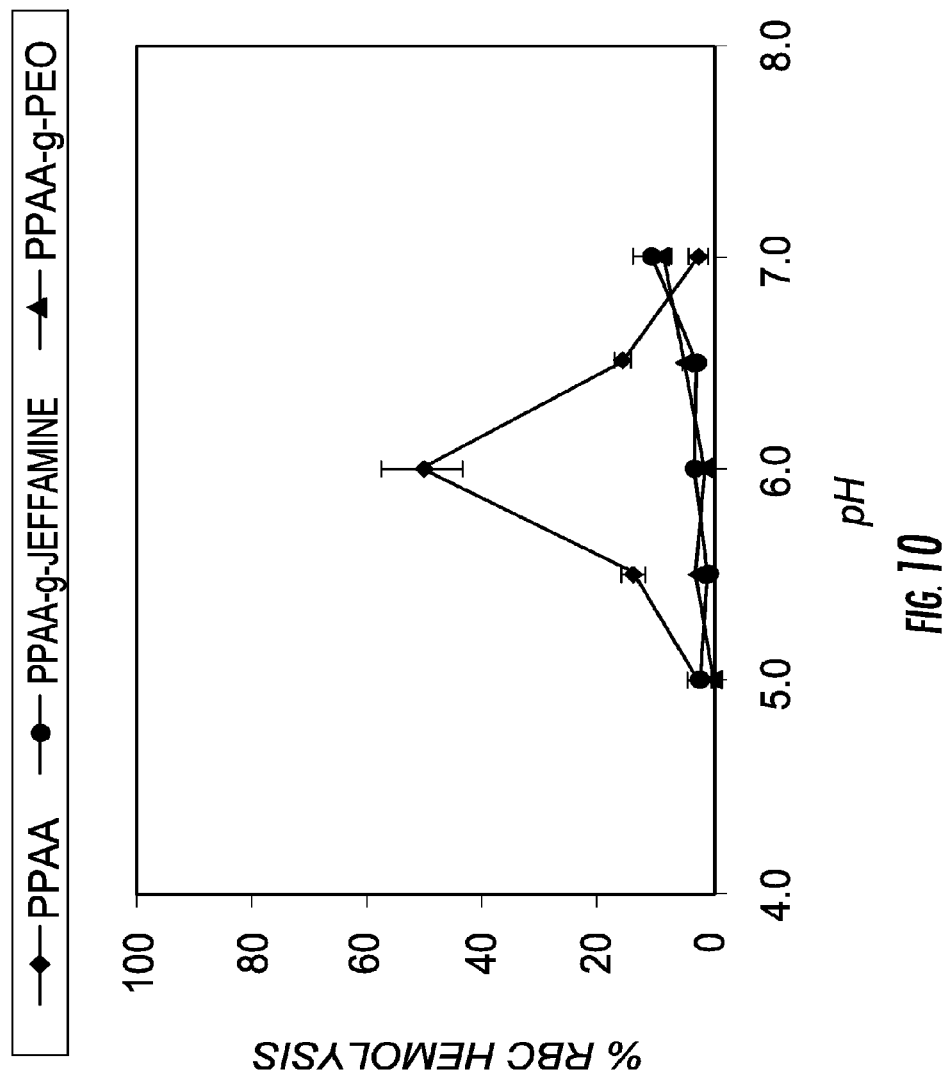
FIG. 10 presents results of studies on hemolysis induced by PPAA and graft copolymers.

RBC hemolysis induced by polymer was normalized to control (distilled water). PPAA produces significant hemolytic activity at pH 6.0, the pH of endosomes, and absence of hemolytic activity at pH 7.0, the pH of the cytoplasm. In comparison, both the graft copolymers, PPAA-g-PEO and PPAA-g-Jeffamine, demonstrate <10% hemolytic activity throughout the pH range of 5.0 to 7.0. The data (mean±SD (n=3)) are presented in FIG. 10.

Intracellular ODN Delivery and Inhibition of d1EGFP Expression.

The biological activity of the ODN complexes was assessed in CHO and U87 cell lines that stably express a target gene encoding d1EGFP, a form of enhanced green fluorescent protein with a protein half-life of approximately 1 hr. The intracellular delivery of ODN molecules into cells and the gene silencing effects were quantitatively determined from the fluorescence of Cy5-labeled ODN and GFP expression, respectively, using flow cytometry.

Cells were split at approximately 70% confluence and seeded onto 12-well plates (Fisher, Suwanee, Ga.) at $10^5$ cells/ml (with 1 ml per well) ~18 h prior to ODN treatment. For cellular uptake and antisense studies, cells were treated with Cy5-labelled antisense ODN (target d1EGFP gene encoding GFP) to result in a final ODN concentration of 300 nM per well. In the case of treatment, 200 μl of complexes were prepared as described in the 'Vector preparation' section, mixed with 10% serum-containing cell culture medium and added to each well, while for the control samples complexes were substituted with 200 μl of PBS. After 4 hours of cell exposure to treatment, complexes were aspirated and cells were refilled with fresh medium. Cells were assayed for Cy5-ODN uptake and GFP activity 24 hrs post-ODN treatment using fluorescence activated cell sorting (FACS).

Cells were prepared for FACS analysis first by washing cells with PBS buffer, followed by the addition of trypsin-EDTA (Invitrogen, Carlsbad, Calif.) to remove cells from the plate surface. Immediately after cell detachment, cell culture medium was added to neutralize the trypsin. Following this, cells were collected in pellet form by centrifugation for 3.5 min at 200 g, resuspended in 150 μl of PBS and maintained on ice until the time of analysis. Cells were analyzed for size (side scatter), granularity (forward scatter), intensity of Cy5 fluorescence (FL4 channel) and intensity of GFP (FL1 channel). Geometric mean fluorescence intensities for 10,000 cells were determined on the FACS Calibur three-laser flow cytometer (BD Biosciences). "Control" refers to DOTAP/ODN only and other groups indicate the polymer added to this combination, except "lipo" refers to delivery with Lipofectamine2000. CellQuest software was used to acquire and analyze the results. After ensuring that the background GFP fluorescence from cells lacking d1EGFP plasmid was negligible, the degree of silencing was calculated using the following formula:

$$\% \text{ Silencing} = \frac{(F_{525,treatment})}{(F_{525,control})} * 100$$

Figure 11A:
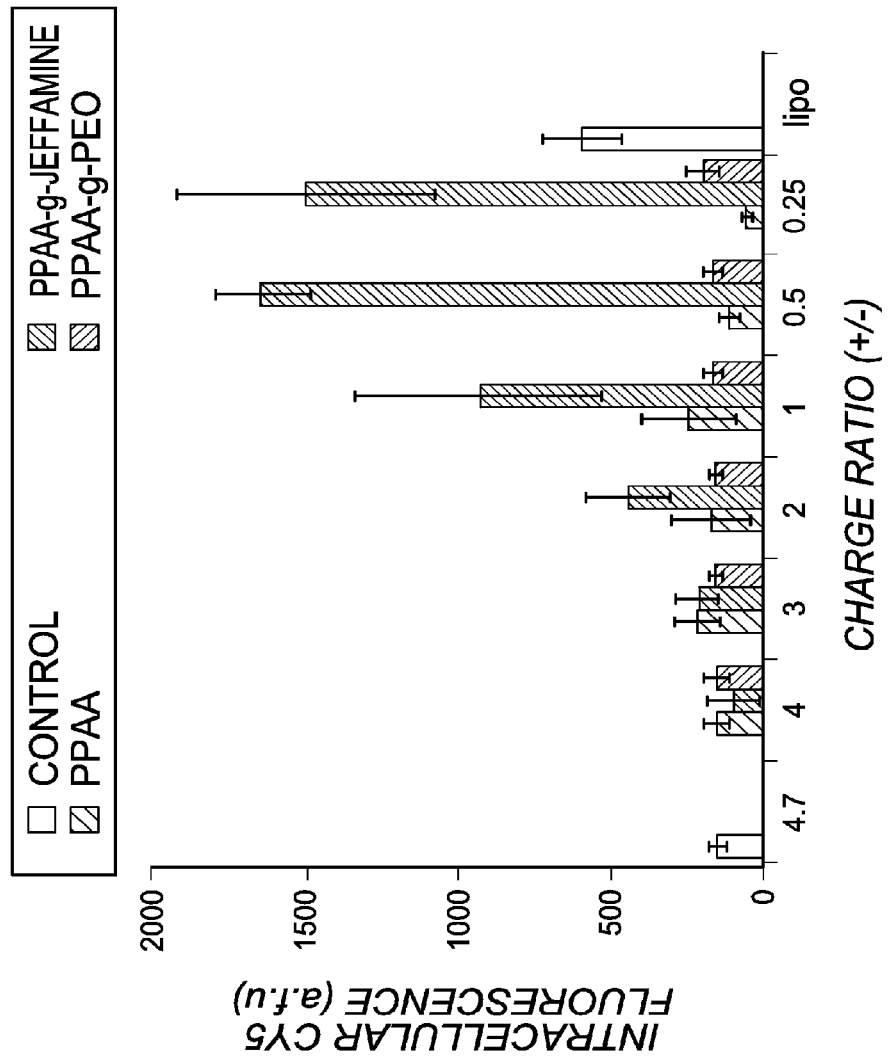
FIGS. 11a and 11b present results of studies on cellular uptake and antisense activity, respectively, of DOTAP/ODN complexes in the presence of PPAA, PPAA-g-Jeffamine or PPAA-g-PEO in CHO-d1EGFP cells 24 hours post-treatment.
Figure 11B:
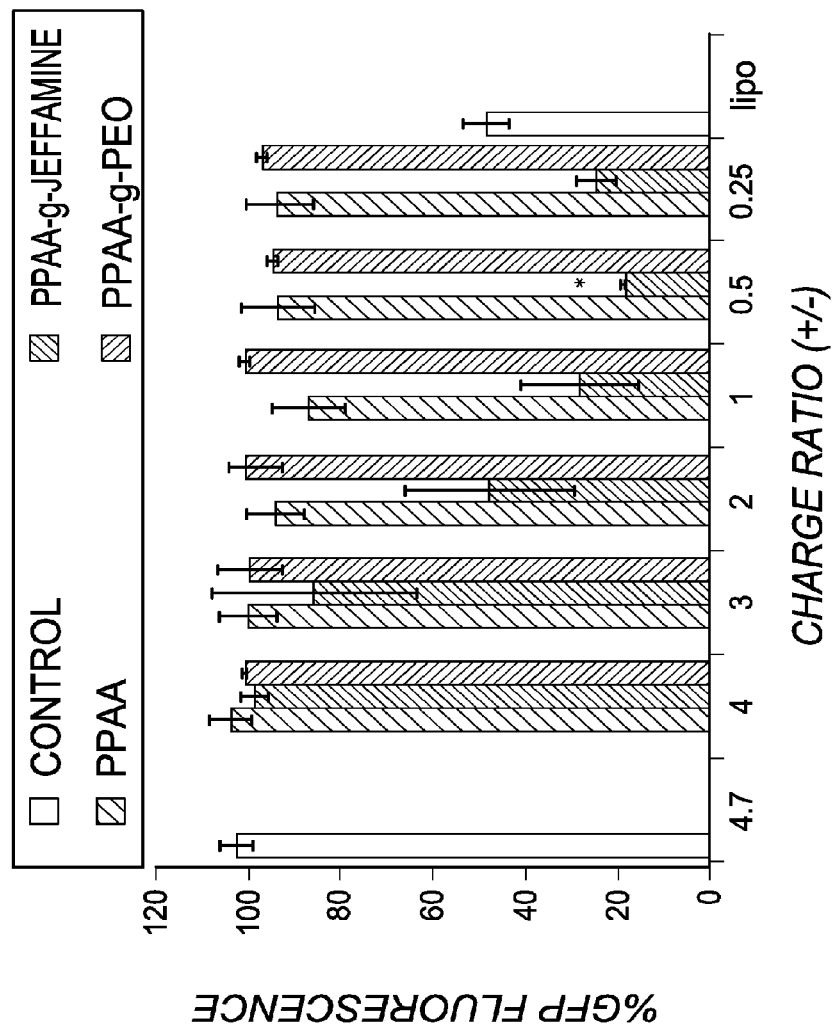

The results for CHO-d1EGFP cell line are presented in FIGS. 11a and 11b. The % GFP Fluorescence is normalized to untreated cells.

In 10% serum-containing media, relatively low levels of Cy5-ODN uptake and minimal antisense activity by the DOTAP/ODN/PPAA complex over a range of charge ratios from 4.7 to 0.25 was observed. The incorporation of PPAA-g-PEO copolymer into DOTAP/ODN complexes also produces no substantial increase in intracellular ODN levels, yielding insignificant antisense activity throughout the range of charge ratios tested. In marked contrast, complexes containing PPAA-g-Jeffamine copolymer produce an 8-fold increase in intracellular levels of ODN compared to PPAA, under the same 10% serum-containing conditions. This enhanced uptake with the PPAA-g-Jeffamine correlates with a gene silencing effect of ~90%. Moreover, PPAA-g-Jeffamine containing complexes deliver ODN and produce a greater antisense effect than the commercial standard, Lipofectamine 2000. The maximum ODN delivery and gene silencing effects induced by PPAA containing complexes occur at a net charge ratio of 1.0, while for PPAA-g-Jeffamine containing complexes the maximum occurs at a net charge ratio of 0.5.

Figure 12A:
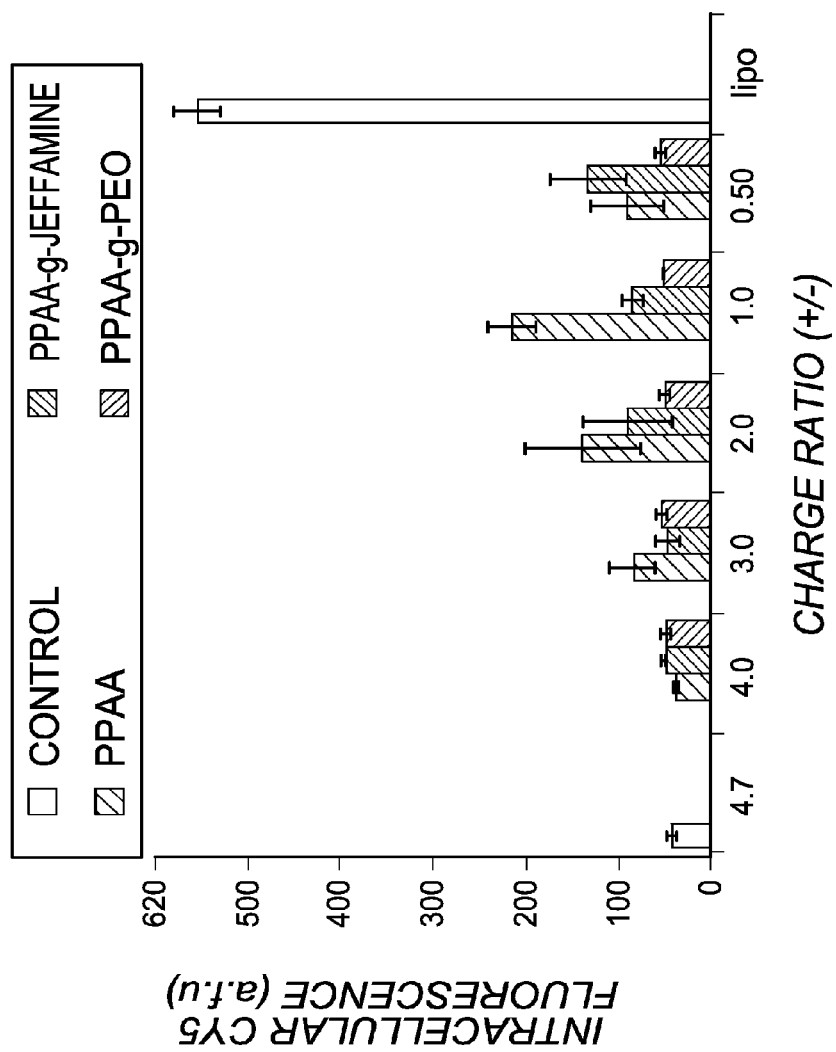
FIGS. 12a and 12b present results of studies on cellular uptake and antisense activity, respectively, of DOTAP/ODN complexes in the presence of PPAA, PPAA-g-Jeffamine or PPAA-g-PEO in U87-d1EGFP cells 24 hours post-treatment.
Figure 12B:
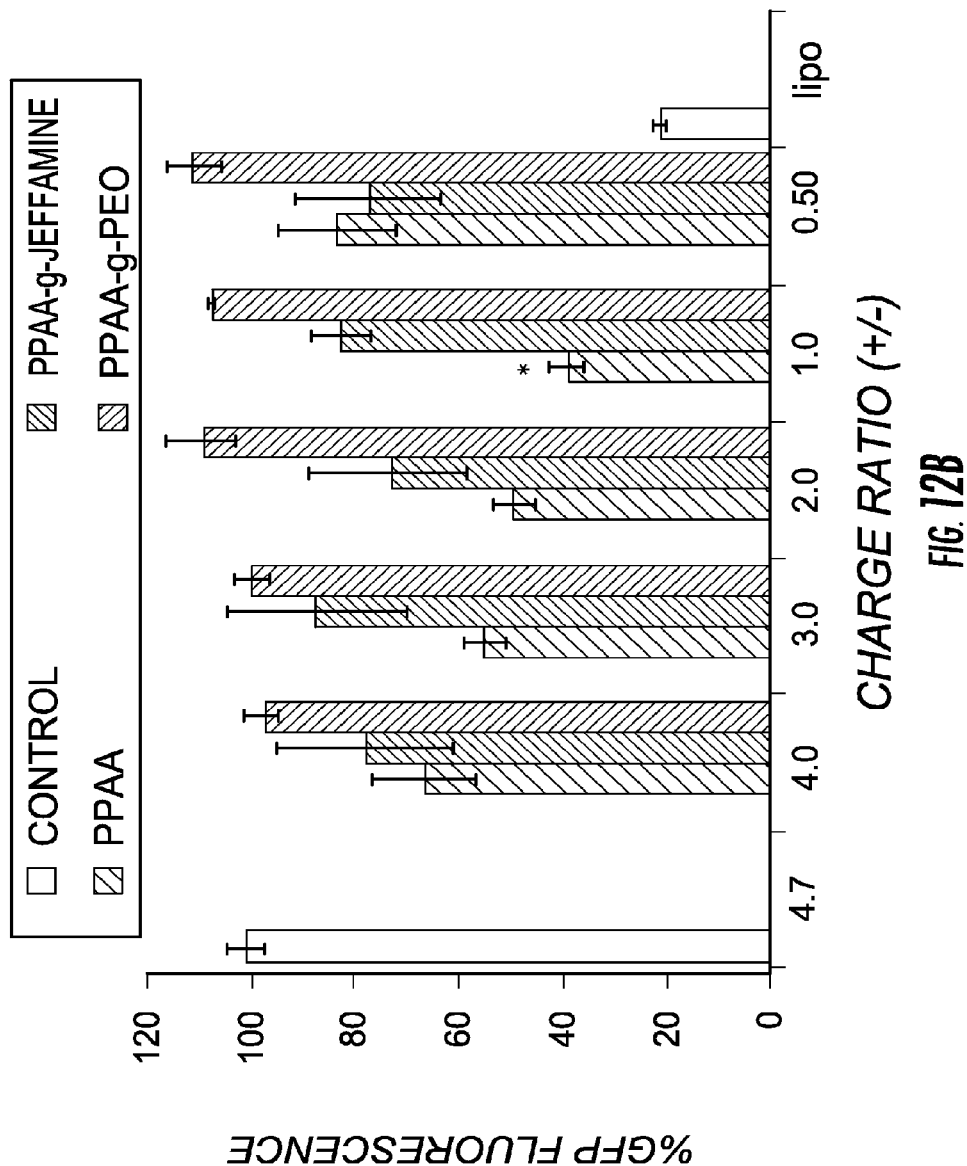

The results for U87-d1EGFP cell line are presented in FIGS. 12a and 12b. In U87-d1EGFP cells, the ability of the various carrier systems to deliver ODN is rather different than that in the CHO-d1EGFP cells. Similar to the results for the CHO-d1EGFP cell line, the DOTAP/ODN delivery system fails to initiate sufficient ODN uptake or significant antisense effect by U87-d1EGFP cells in the presence of serum. In this case, PPAA by itself is the most effective adjunct in treatments with serum-containing media in terms of ODN delivery and gene silencing activity. The PPAA-containing complexes cause a 4-fold increased uptake of ODNs, which results in 60% GFP fluorescence level (or 40% gene silencing) compared to control. Here, the maximum ODN delivery into cells occurs at a net charge ratio of 1. In the case of complexes containing PPAA-g-PEO, we see low levels of intracellular ODN uptake and negligible gene silencing effects. PPAA-g-Jeffamine containing complexes produce a two-fold increased uptake of ODNs compared to complexes without any polymer addition (i.e., DOTAP/ODN), and 30% gene silencing. The PPAA-g-Jeffamine containing complexes achieve maximum antisense activity at a charge ratio of 2, compared to a charge ratio of 0.5 in CHO-d1EGFP cells.

Cytotoxicity/Cell Proliferation

CHO-d1EGFP cells were seeded onto a 96-well plate and treated with 20 µL of complexes, prepared according to methods described above, and mixed with 80 µL of serum-containing media (10% FBS). After 24 hours, 20 µL of MTT reagent (Promega, Madison, Wis.) was added to 100 µL of media, per the manufacturer's protocol, and cells were incubated for a period of two hours under humidified conditions. Production of the tetrazolium salt (MTT) was quantified colorimetrically to represent cell viability, as follows:

$$\% \text{ Cell Viability} = \frac{A_{490,treatment}}{A_{490,control}} * 100$$

Figure 13A:
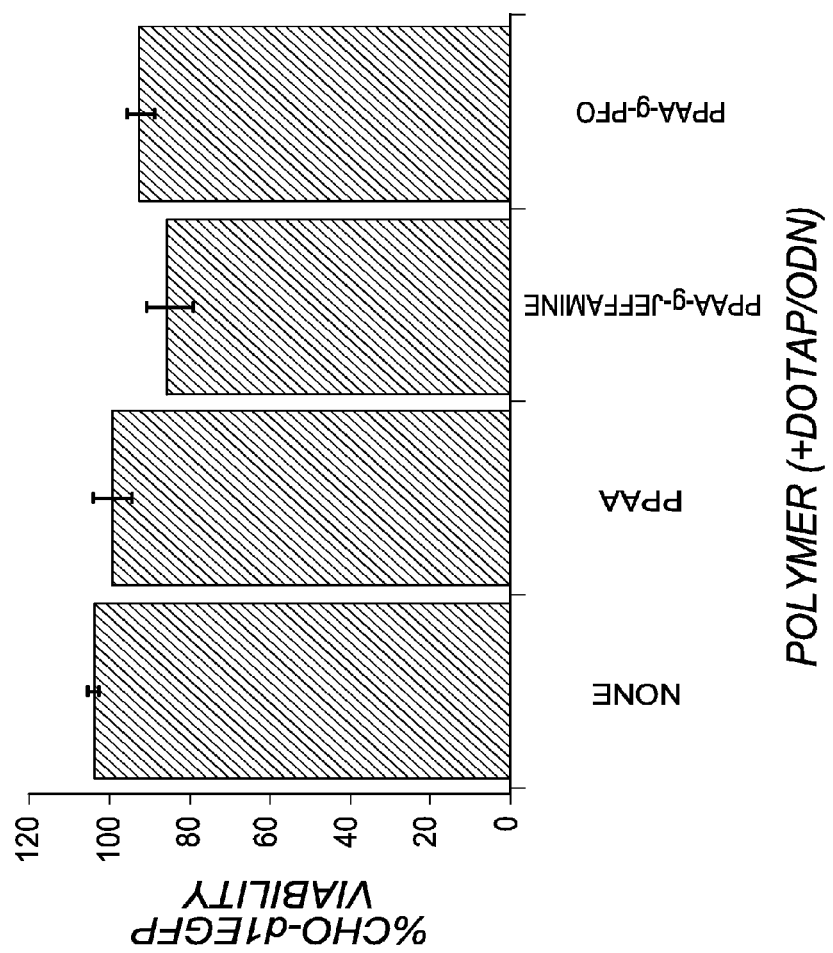
FIGS. 13a and 13b present results of studies on effect of PPAA, PPAA-g-Jeffamine and PPAA-g-PEO containing complexes on CHO-d1EGFP and U87-d1EGFP cell viability, respectively.
Figure 13B:
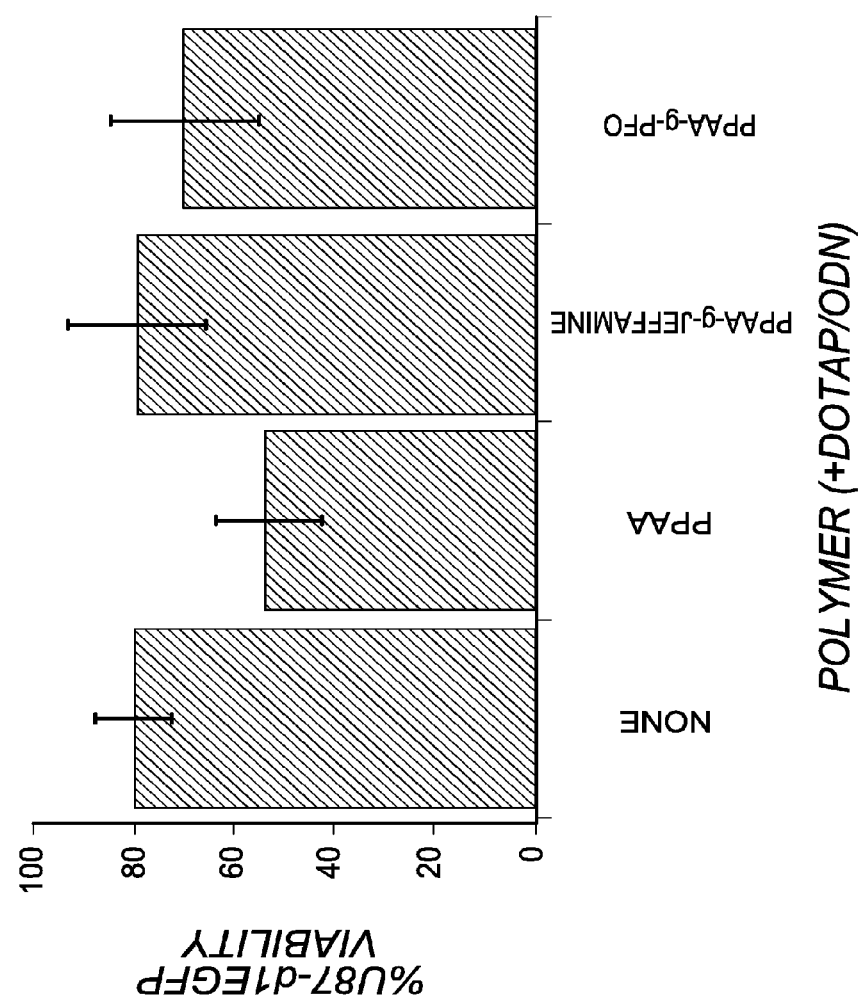

The results for the cytotoxicity study CHO-d1EGFP cells and U87-d1EGFP cells are presented in FIG. 13a and FIG. 13b, respectively. In both CHO-d1EGFP and U87-d1EGFP cell lines the greatest cytotoxicity is induced by the complex that yields highest ODN delivery and antisense activity (FIG. 6). That is, in CHO-d1EGFP cells, the PPAA-g-Jeffamine containing complex is the most cytotoxic at the optimal charge ratio of 0.5, although the effect is relatively small (cell viability exceeds 80%). Similarly, in U87-d1EGFP cells, the PPAA containing complex is the most cytotoxic (cell viability reduced to about 50%) at the optimal charge ratio of 1.0.

Example 3

Silencing of Oncogene Expression in Cancer Cells by Delivery of siRNA with Graft Copolymer Formulation Ability of graft copolymers to enhance cationic liposome-mediated delivery of siRNAs that is targeted to Bcl-2, anti-apoptotic, gene was tested. The degree of Bcl-2 gene silencing was assessed in HeLa (cervical carcinoma) and MCF-7 (breast cancer) cell lines that over-expressing this oncogene.

Cells were seeded in 12-well plates at ~$10^5$ cells/ml and treated with siRNA-containing complexes (at a final siRNA concentration of 40 and 50 nM) 20 hours post-seeding. The cells were treated with complexes for a period of 4 hours under serum-containing (10% FBS) media, after which complexes were aspirated and replaced with fresh media. We evaluate the degree of mRNA gene silencing 24 hours post-treatment using PCR (polymerase chain reaction) by the 2ΔΔ$C_T$ method. This method assumes equal amplification efficiencies for b-actin and Bcl-2 gene.

The degree of gene silencing was calculated using the following equations:

$$\Delta C_T = (C_T)_{Bcl-2} - (C_T)_{\beta-actin}$$

$$\Delta\Delta C_T = (C_T)_{treatment} - (C_T)_{control}$$

$$\% \text{ Silencing} = 100 - (2^{-\Delta\Delta C_T} * 100)$$

The degree of gene silencing in HeLa cell type (cervical carcinoma) observed 24 hours after treatment with siRNA at concentration of 40 nM using various siRNA delivery methods are presented in Table 6 below.

TABLE 6

The degree of gene silencing in HeLa cell type

| Sample | $(C_T)_{\beta-actin}$ | $(C_T)_{Bcl-2}$ | $\Delta C_T$ | $\Delta\Delta C_T$ | % Silencing |
|---|---|---|---|---|---|
| Control | 11.9 | 25.6 | 13.6 | | |
| Lipofectamine 2000/siRNA | 11.8 | 26.2 | 14.4 | 0.8 | 42.6 |
| DOTAP/PPAA/siRNA | 12.4 | 27.0 | 14.5 | 0.9 | 46.0 |
| DOTAP/PPAA-g-Jeffamine/siRNA | 12.1 | 27.1 | 15.0 | 1.4 | 61.0 |

The degree of gene silencing in MCF-7 cell type (breast tumor) observed 24 hours after treatment with siRNA at concentration of 50 nM using various siRNA delivery methods are presented in Table 7 below.

TABLE 7

The degree of gene silencing in MCF-7 cell type

| Sample | $(C_T)_{\beta\text{-}actin}$ | $(C_T)_{Bcl\text{-}2}$ | $\Delta C_T$ | $\Delta\Delta C_T$ | % Silencing |
|---|---|---|---|---|---|
| Control | 10.2 | 21.9 | 11.6 | | |
| Lipofectamine 2000/siRNA | 10.1 | 21.9 | 11.9 | 0.25 | 15.9 |
| DOTAP/PPAA/siRNA | 10.3 | 22.0 | 11.7 | 0.1 | 6.0 |
| DOTAP/PPAA-g-Jeffamine/siRNA | 10.1 | 22.6 | 12.5 | 0.9 | 46.4 |

The degree of gene silencing in MCF-7 cell type (breast tumor) observed 24 hours after treatment with siRNA at concentration of 100 nM using various siRNA delivery methods are presented in FIG. 14.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. A graft polymer comprising:
   a backbone comprising a poly(alkyl acrylic acid); and
   one or more pendent chains comprising one or more polyetheramine moieties covalently attached to said polymer backbone via said acrylic acid groups;
   wherein a majority of the ether groups of said polyetheramine moieties comprise ethylene oxide repeating units; and
   wherein said polymer has a graft density between about 1 and about 25 mole percent.

2. The graft polymer of claim 1, wherein the backbone comprises poly(propyl acrylic acid).

3. The graft polymer of claim 1 having a graft density between about 5 and about 25 mole percent.

4. The graft polymer of claim 1, wherein said one or more polyetheramine moieties are amphipathic.

5. The graft polymer of claim 1, wherein said polyetheramine moieties have a molecular weight between about 200 and about 5,000 Daltons.

6. The graft polymer of claim 1, wherein said polyetheramine moieties further comprise propylene oxide moieties.

7. The graft polymer of claim 2 having a graft density between about 5 and about 25 mole percent.

8. The graft polymer of claim 2, wherein said one or more polyetheramine moieties are amphipathic.

9. The graft polymer of claim 2, wherein said polyetheramine moieties have a molecular weight between about 200 and about 5,000 Daltons.

10. The graft polymer of claim 2, wherein said polyetheramine moieties further comprise propylene oxide moieties.

11. The graft polymer of claim 1, having a graft density between 10 and 25 mole percent.

12. The graft polymer of claim 2, having a graft density between 10 and 25 mole percent.

13. The graft polymer of claim 6, wherein the propylene oxide:ethylene oxide ratio is about 10 to about 31.

14. The graft polymer of claim 10, wherein the propylene oxide:ethylene oxide ratio is about 10 to about 31.

* * * * *